(12) United States Patent
Otterbein et al.

(10) Patent No.: US 9,522,163 B2
(45) Date of Patent: Dec. 20, 2016

(54) METHODS OF TREATING HEPATITIS

(71) Applicants: University of Pittsburgh—Of the Commonwealth System of Higher Education, Pittsburgh, PA (US); Yale University, New Haven, CT (US)

(72) Inventors: Leo E. Otterbein, Beverly, MA (US); Augustine M. K. Choi, Pittsburgh, PA (US); Brian Scott Zuckerbraun, Pittsburgh, PA (US)

(73) Assignees: University of Pittsburgh—Of the Commonwealth System of Higher Education, Pittsburgh, PA (US); Yale University, New Haven, CT (US)

( * ) Notice: Subject to any disclaimer, the term of this patent is extended or adjusted under 35 U.S.C. 154(b) by 0 days.

(21) Appl. No.: 14/094,140

(22) Filed: Dec. 2, 2013

(65) Prior Publication Data
US 2014/0141103 A1    May 22, 2014

Related U.S. Application Data

(63) Continuation of application No. 13/803,330, filed on Mar. 14, 2013, now abandoned, which is a continuation of application No. 13/544,701, filed on Jul. 9, 2012, now abandoned, which is a continuation of application No. 10/439,632, filed on May 16, 2003, now abandoned.

(60) Provisional application No. 60/381,527, filed on May 17, 2002.

(51) Int. Cl.
*A61K 33/00* (2006.01)
*A61P 1/16* (2006.01)
*A61K 45/06* (2006.01)

(52) U.S. Cl.
CPC ............... *A61K 33/00* (2013.01); *A61K 45/06* (2013.01)

(58) Field of Classification Search
None
See application file for complete search history.

(56) References Cited

U.S. PATENT DOCUMENTS

| | | |
|---|---|---|
| 4,053,590 A | 10/1977 | Bonsen et al. |
| 4,264,739 A | 4/1981 | Grabner et al. |
| 4,923,817 A | 5/1990 | Mundt |
| 5,084,380 A | 1/1992 | Carney |
| 5,180,366 A | 1/1993 | Woods |
| 5,240,912 A | 8/1993 | Todaro |
| 5,293,875 A | 3/1994 | Stone |
| 5,449,665 A | 9/1995 | Sollevi |
| 5,476,764 A | 12/1995 | Bitensky |
| 5,498,421 A | 3/1996 | Grinstaff et al. |
| 5,632,162 A | 5/1997 | Billy |
| 5,664,563 A | 9/1997 | Schroeder et al. |
| 5,702,325 A | 12/1997 | Watterson et al. |
| 5,731,326 A | 3/1998 | Hart et al. |
| 5,763,431 A | 6/1998 | Jackson |
| 5,792,325 A | 8/1998 | Richardson, Jr. |
| 5,876,604 A | 3/1999 | Nemser et al. |
| 5,882,674 A | 3/1999 | Herrmann et al. |
| 5,885,621 A | 3/1999 | Head et al. |
| 5,914,316 A | 6/1999 | Brown et al. |
| 6,066,333 A | 5/2000 | Willis et al. |
| 6,069,132 A | 5/2000 | Revanker et al. |
| 6,158,434 A | 12/2000 | Lugtigheid et al. |
| 6,203,991 B1 | 3/2001 | Nabel et al. |
| 6,313,144 B1 | 11/2001 | McCullough et al. |
| 6,316,403 B1 | 11/2001 | Pinsky et al. |
| 7,011,854 B2 | 3/2006 | Haas et al. |
| 7,045,140 B2 | 5/2006 | Motterlini et al. |
| 7,238,469 B2 | 7/2007 | Bach et al. |
| 7,364,757 B2 | 4/2008 | Otterbein et al. |
| 7,678,390 B2 | 3/2010 | Choi et al. |
| 7,687,079 B2 | 3/2010 | Otterbein et al. |
| 7,691,416 B2 | 4/2010 | Otterbein et al. |
| 2002/0033174 A1 | 3/2002 | Lecourt et al. |
| 2002/0155166 A1 | 10/2002 | Choi et al. |
| 2003/0009127 A1 | 1/2003 | Trescony et al. |
| 2003/0039638 A1 | 2/2003 | Bach et al. |
| 2003/0064114 A1 | 4/2003 | Motterlini et al. |
| 2003/0068387 A1 | 4/2003 | Buelow et al. |
| 2003/0219496 A1 | 11/2003 | Otterbein et al. |
| 2003/0219497 A1 | 11/2003 | Otterbein et al. |
| 2004/0005367 A1 | 1/2004 | Otterbein et al. |
| 2004/0067261 A1 | 4/2004 | Haas et al. |
| 2004/0131703 A1 | 7/2004 | Bach et al. |
| 2004/0197271 A1 | 10/2004 | Kunka et al. |
| 2004/0228930 A1 | 11/2004 | Billiar et al. |
| 2004/0258772 A1 | 12/2004 | Otterbein et al. |

(Continued)

FOREIGN PATENT DOCUMENTS

FR       2 816 212      5/2002
JP       56079957 A     6/1981

(Continued)

OTHER PUBLICATIONS

Abidin et al., "The Combined Effect of Carbon Monoxide and Normobaric Hyperoxia on Animals", Kosmicheskaya Biologiya I Aviakosmicheskaya Meditsina 6: 63-67 (1978).

(Continued)

*Primary Examiner* — Abigail Fisher
*Assistant Examiner* — Frank Choi
(74) *Attorney, Agent, or Firm* — Fish & Richardson P.C.

(57) ABSTRACT

The present invention relates to a method of treating hepatitis in a patient, which includes administering a pharmaceutical composition that includes carbon monoxide to the patient.

8 Claims, 20 Drawing Sheets
(3 of 20 Drawing Sheet(s) Filed in Color)

(56) References Cited

U.S. PATENT DOCUMENTS

| | | |
|---|---|---|
| 2005/0048133 A1 | 3/2005 | Pinsky et al. |
| 2005/0215468 A1 | 9/2005 | Bar-Or et al. |
| 2005/0250688 A1 | 11/2005 | Pinsky et al. |
| 2005/0255178 A1 | 11/2005 | Bloch et al. |
| 2006/0003922 A1 | 1/2006 | Bach et al. |
| 2007/0202083 A1 | 8/2007 | Bach et al. |

FOREIGN PATENT DOCUMENTS

| | | |
|---|---|---|
| WO | WO 94/22482 | 10/1994 |
| WO | WO 95/35105 | 12/1995 |
| WO | WO 98/08523 | 3/1998 |
| WO | WO 98/13058 | 4/1998 |
| WO | WO 99/49880 | 4/1999 |
| WO | WO 99/47512 | 9/1999 |
| WO | WO 02/09731 | 2/2002 |
| WO | WO 02/078684 | 10/2002 |
| WO | WO 02/092075 | 11/2002 |
| WO | WO 03/000114 | 1/2003 |
| WO | WO 03/066067 | 8/2003 |
| WO | WO 03/072024 | 9/2003 |
| WO | WO 03/088748 | 10/2003 |
| WO | WO 03/088923 | 10/2003 |
| WO | WO 03/088981 | 10/2003 |
| WO | WO 03/009493 | 11/2003 |
| WO | WO 03/096977 | 11/2003 |
| WO | WO 03/103585 | 12/2003 |
| WO | WO 2004/000368 | 12/2003 |
| WO | WO 2004/004817 | 1/2004 |
| WO | WO 2004/043341 | 5/2004 |

OTHER PUBLICATIONS

Akamatsu et al., "Heine oxygenase-1-derived carbon monoxide protects hearts from transplant associated ischemia reperfusion injury," FASEB J., 18:771-772 (2004).

Allred et al., "Effects of Carbon Monoxide on Myocardial Ischemia," Environmental Health Perspectives 91:89-132 (1991).

American Thoracic Society, "Single breath carbon monoxide diffusing capacity (transfer factor): recommendations for a standard technique," Am. Rev. Respir. Dis. 136:1299-1307 (1987).

American Thoracic Society, "Single breath carbon monoxide diffusing capacity (transfer factor): recommendations for a standard technique-1995 update," Am. J. Respir. Crit. Care. Med. 152:2185-2198 (1995).

Appel et al., "The pig as a source of Cardiac xenografts," J. Card. Surg. 16:345-56 (2001).

Arcasoy et al., "Erythropoietin (EPO) Stimulates Angiogenesis in Vivo and Promotes Wound Healing," Blood 98:822A-823A, Abstract (2001).

Arita et al., "Prevention of Primary Islet Isograft Nonfunction in Mice with Pravastatin," Transplantation 65:1429-33 (1998).

Arnush et al., "IL-1 Produced and Released Endogenously within Human Islets Inhibits β Cell Function," J. Clin Invest. 102:516-26 (1998).

Bach et al., "Accommodation of vascularized xenografts: Expression of "protective genes" by donor endothelial cells in a host Th2 cytokine environment," Nature Med. 3:196-204 (1997).

Bach, "Heme oxygenase-1 as a protective gene," Wien. Klin. Wochenschr. 114(Suppl):4:1-3 (2002).

Baim and Grossman, "Treatment of Coronary Stenoses and Occlusions with Coronary Angioplasty," Harrison's Principles of Internal Medicine, 13th Ed., vol. 1, 193:986-87 (1994).

Bartholomew, G.W. and M. Alexander, "Microbial metabolism of carbon monoxide in culture and in soil," Appl. Environ. Microbiol., 37(5):932-937 (1979).

Bathoorn et al., "Anti-inflammatory effects of inhaled carbon monoxide in patients with COPD: a pilot study," Eur. Respir. J. 0: 09031936.00163206v1 (Aug. 22, 2007).

Bathoorn et al., "Effects of low dose inhaled carbon monoxide in patients with COPD," Eur. Respir. J., 28(Suppl. 50):661s (2006).

Bauer et al., "Bench-to-bedside review: carbon monoxide-from mitochondrial poisoning to therapeutic use," Crit. Care, 13:220 (2009).

Bauer et al., "Transcriptional activation of heme oxygenase-1 and its functional significance in acetaminophen-induced hepatitis and hepatocellular injury in the rat," J. Hepatol., 33:395-406 (2000).

Bentley et al., "Successful Cardiac Transplantation with Methanol or Carbon Monoxide-Poisoned Donors," Thorac Surg 71(4):1194-7 (2001).

Berney et al., "Islet cell transplantation: the future?" Langenbeck's Arch. Surg. 385: 373-8 (2000).

Billiar, "The diverging roles of carbon monoxide and nitric oxide in resuscitated hemorrhagic shock," Crit. Care Med. 27:2842-3 (1999).

Bishop, G.A. et al., "Spontaneous acceptance of liver transplants in rodents: evidence that liver leucocytes induce recipient T-cell death by neglect," Immunol. Cell Biol., 80(1):93-100 (2002).

Bracho et al., "Carbon Monoxide Protects against Organ Injury in Hemorrhagic Shock/Resuscitation," Journal of Surgical Research, 107:270, (2002), Abstract.

Brouard et al., "Carbon monoxide generated by Heme Oxygenase-1 (HO-1) suppresses endothelial cell apoptosis via activation of the p38 mitogen activated protein kinase (MAPK) pathway," Acta Haematologica 103(Suppl 1):64, (2000), Abstract.

Brouard et al., "Carbon Monoxide Generated by Heme Oxygenase-1 Suppresses Endothelial Cell Apoptosis," J Exp Med 192(7):1015-25 (2000).

Brouard et al., "Heme oxygenase-1-derived carbon monoxide requires the activation of transcription factor NF-kappa B to protect endothelial cells from tumor necrosis factor-alpha-mediated apoptosis," J. Biol. Chem., 277(20):17950-17961, (2002).

Brouard et al., "Molecular mechanism underlying the anti-apoptotic effect of Heme oxygenase-1 derived carbon monoxide," Xenotransplantation, 8(Suppl 1): p. 22 (2001).

Brown et al., "In vivo binding of carbon monoxide to cytochrome c oxidase in rat brain", American Physiological Society, pp. 604-610 (1990).

Calabrese et al., "Carbon Monoxide (CO) Prevents Apoptotic Events Related to Ischemia/Reperfusion (IR) Injury in an hDAF Pig-to-Primate Xenotransplantation Model," Xenotransplantation 10:488, (2003), Abstract.

Campbell, "Living at Very High Altitudes", The Lancet 1:370-373 (1930).

Campbell, "The Effect of Carbon Monoxide and Other Agents Upon the Rate of Tumour Growth", J Pathology & Bacteriology 35:379-394 (1932).

Campell, "Cancer of Skin and Increase in Incidence of Primary Tumours of Lung in Mice Exposed to Dust Obtained from Tarred Roads", Brit. J Exper. Pathol. XV(5):24, 289-294 (1934).

Cantrell et al., "Low-Dose Carbon Monoxide Does Not Reduce Vasoconstriction in Isolated Rat Lungs", Experimental Lung Research 22:21-32 (1996).

Caplan et al., "Role of asphyxia and feeding in a neonatal rat model of necrotizing enterocolitis," Pediatr. Pathol., 14:1017-1028 (1994).

Carbon Monoxide Poisoning—Symptoms; http://my.webmd.com/hw/home_health/aa7304.asp;retrieved Jul. 11, 2005.

Carbon Monoxide Poisoning—What Happens; http://my.webmd.com/hw/home_health/aa7326.asp;retrieved Jul. 11, 2005.

Carbon Monoxide to Prevent Lung Inflammation, http://www.clinicaltrials.gov/ct/show/NCT00094406?order=2 (retrieved on Aug. 28, 2006).

Cardell et al., "Bronchondilatation in vivo by carbon monoxide, a cyclic GMP related messenger", British J. of Pharmacology 124:1065-1068 (1998).

Carlsson et al., "Measurements of Oxygen Tension in Native and Transplanted Rat Pancreatic Islets," Diabetes 47:1027-32 (1998).

Carraway et al., "Induction of ferritin and heme oxygenase-1 by endotoxin in the lung", Am J Physiol Lung Cell Mol Physiol 275:L583-592 (1998).

Cecil Textbook of Medicine (21st Ed. 2000) 1:273-279, 357-372, 387-419, 425-427, 436-448, 466-475, 507-512, 1060-1074.

(56) References Cited

OTHER PUBLICATIONS

Cecil Textbook of Medicine (21$^{st}$ Ed. 2000) 2:1492-1499, 2042-2047, 2079-2081.
Chapman and Choi, "Exhaled monoxides as a pulmonary function test: use of exhaled nitric oxide and carbon monoxide," Clin. Chest Med. 22:817-836 (2001).
Chapman et al., "Carbon Monoxide Attenuates Aeroallergen-induced Inflammation in Mice", *Am. J. Physiol. Lung Cell Mol Physiol.* 281:L209-L216 (2001).
Chapman et al., "Exogenous Carbon Monoxide Attenuates Aeroallergen-induced Eosinophilic Inflammation in Mice", *J Respiratory Critical Care Med* 159(3):A218 (1999).
Chapter 5.5, Carbon Monoxide, WHO Regional Office for Europe, Copenhagen, Denmark, pp. 1-15 (2000).
Chin et al., "Transcriptional regulation of the HO-1 gene in cultured macrophages exposed to model airborne particulate matter," Am. J. Physiol. Lung Cell. Mol. Physiol., 284(3):L473-L480, (2003).
Choi and Otterbein, "Emerging role of carbon monoxide in physiologic and pathophysiologic states," Antioxid. Redox Signal. 4:227-228 (2002).
Choi et al., "'Therapeutic' carbon monoxide may be a reality soon," Am. J. Respir. Crit. Care Med., 171(11):1318-1319 (2005).
Choi et al., "Heme Oxygenase-1: Function, Regulation, and Implication of a Novel Stress-inducible Protein in Oxidant-induced Lung Injury", *Am. J Respir. Cell Mol. Biol.* 15:9-19 (1996).
Choi, "Heme Oxygenase-1 Protects the Heart," Circulation Research 89:105-107 (2001).
Christodoulides et al., "Vascular Smooth Muscle Cell Heme Oxygenases Generate Guanylyl Cyclase-Stimulatory Carbon Monoxide," *Circulation* 97:2306-9 (1995).
Clayton et al., "Inhaled carbon monoxide and hyperoxic lung injury in rats," Am. J. Physiol. Lung Cell Mol. Physiol. 281:L949-57 (2001).
Corbett et al., "Nitric oxide mediates cytokine-induced inhibition of insulin secretion by human islets of Langerhans," *Proc. Natl. Acad. Sci USA* 90:1731-5 (1993).
Cozzi et al., "Donor Preconditioning with Carbon Monoxide (CO) in Pig-to-Primate Xenotransplantation," Xenotransplantation 10:528, (2003), Abstract.
Crapo et al., "Single-breath carbon monoxide diffusing capacity," Clin. Chest Med., 22:637-649, (2001).
Czlonkowska et al, "Immune processes in the pathogenesis of Parkinson's disease—a potential role for microglia and nitric oxide," Med. Sci. Monit. 8:RA165-RA177 (2002).
Datta, R. and J.G. Zeikus, "Modulation of Acetone-Butanol-Ethanol Fermentation by Carbon Monoxide and Organic Acids," *Appl. Environ. Microbiol.*, 49(3):522-529 (1985).
Davidson et al., "Inflammatory Modulation and Wound Repair" *J Investigative Dermatology* xi-xii (2003).
Deng et al., "Carbon Monoxide Potentiates Cerulein-Induced Pancreatitis in Chronic Alcohol-Fed Rats," Gastroenterology, 124(4):A618-19, (2003), Abstract.
Dioum et al., "NPAS2: A Gas-Responsive Transcription Factor", Sciencexpress/www.sciencexpress.org/21 November 2002/pages 1-6/10.1126/science.1078456.
Dolinay et al., "Can Inhalation Carbon Monoxide be utilized as a therapeutic modality in human diseases?", pp. 203-236 in Breath Analysis for Clinical Diagnosis and Therapeutic Monitoring, Amann and Smith, eds., World Scientific Publishing Company (2004).
Dolinay et al., "Inhaled carbon monoxide confers antiinflammatory effects against ventilator-induced lung injury," Am. J. Respir. Crit. Care Med. 170:613-20 (2004).
Donnelly et al., "Expression of Heme-Oxygenase in Human Airway Primary Epithelial Cells", *J Respiratory Critical Care Med* 159(3):A218 (1999).
Dulak et al., "Carbon monoxide—a 'new' gaseous modulator of gene expression," Acta Biochim. Polonica, 50:31-47 (2003).

Dumortier et al., "Hepatitis B virus reactivation with live failure successfully treated with corticosteroids, foscarnet and ganciclovir," Gastroenterol. Clin. Biol., 21(12):982-986 (1997).
Dyck et al., "Carbon Monoxide (CO) Attenuates Lipopolysaccharide (LPS)-Induced Cytokine Expression of IL-6," Acta Haematologica 103(Suppl 1):64, (2000), Abstract.
Ellenhorn and Barceloux, "Carbon Monoxide" in *Medical Toxicology, Diagnosis and Treatment of Human Poisoning* (New York, New York) pp. 820-829 (1988).
Farrugia and Szurszewski, "Heme oxygenase, carbon monoxide, and interstitial cells of Cajal," Microsc. Res. Tech. 47:321-4, (1999).
Favory et al., "Myocardial Dysfunction and Potential Cardiac Hypoxia in Rats Induced by Carbon Monxide Inhalation," Am. J. Respir. Crit. Care Med. 174:320-25 (2006).
Friebe et al., "YC-1 Potentiates Nitic Oxide- and Carbon Monoxide-Induced Cyclic GMP Effects in Human Platelets", Molecular Pharmacology 54: 962-967 (1998).
Fujita et al., "Paradoxical rescue from ischemic lung injury by inhaled carbon monoxide driven by derepression of fibrinolysis," Nature Medicine 7:598-604 (2001).
Gaine et al., "Induction of Heme Oxygenase-1 with Hemoglobin Depresses Vasoreactivity in Rat Aorta," *J Vasc Res* 36(2):114-9 (1999).
Goldberg and Schneider, "Similarities between the oxygen-sensing mechanisms regulating the expression of vascular endothelial growth factor and erythropoietin," J. Biol. Chem. 269:4355-359 (1994).
Grau et al., "Effect of Carbon Monoxide Breathing on Hypoxia and Radiation Response in the SCCVII Tumor in vivo", *Int. J. Radiation Oncology Biol. Phys.* 29:449-454 (1994).
Grau et al., "Influence of Carboxyhemoglobin Level on Tumor Growth, Blood Flow, and Radiation Response in an Experimental Model," *Int. J. Radiation Oncology Biol. Phys.* 22:421-424 (1992).
Günther et al., "Carbon monoxide protects pancreatic beta-cells from apoptosis and improves islet function/survival after transplantation," Diabetes, 51(4):994-999, (2002).
Guo, "The Research Status of the Gas Messenger Molecules of Nitric Oxide and Carbon Monoxide in the Biomedicine Field," Practical Journal of Cardiac, Cerebral and Pulmonary Vascular Diseases vol. 8(2) (2000) (English translation included).
Hantson et al., "Organ Transplantation From Victims of Carbon Monoxide Poisoning," *Ann Emerg Med* 27(5):673-4 (1996).
Harbrecht et al , "Inhibition of nitric oxide synthase during hemorrhagic shock increases hepatic injury," Shock, 4:332-337 (1995).
Harbrecht et al , "Inhibition of nitric oxide synthesis during severe shock but not after resuscitation increases hepatic injury and neutrophil accumulation in hemorrhaged rats," Shock, 8:415-421 (1997).
Harmey and Bouchier-Hayes, "Vascular endothelial growth factor (VEGF), a survival factor for tumour cells: implications for anti-angiogenic therapy," Bioessays 24:280-83 (2003).
Hartsfield and Choi, "Mitogen activated protein kinase (MAPK) is modulated by both endogenous and exogenous carbon monoxide," FASEB Journal 12:A187, 1088, (1998), Abstract.
Hartsfield et al., "Differential signaling pathways of HO-1 gene expression in pulmonary and systemic vascular cells," Am. J. Physiol., 277(6 Pt 1):L1133-L1141, (1999).
Hartsfield et al., "Regulation of heme oxygenase-1 gene expression in vascular smooth muscle cells by nitric oxide," Am. J. Physiol., 273(5 Pt 1):L980-988, (1997).
Hartsfield, "Cross talk between carbon monoxide and nitric oxide," Antioxid. Redox Signal. 4:301-307 (2002).
Hartsfield, "Targeted Overexpression of Heme Oxygenase-1 (HO-1) Attenuates Hypoxia-Induced Right Ventricular Hypertrophy," FASEB Journal 13:A827, (1999), Abstract.
Haschemi et al., "Cross-regulation of carbon monoxide and the adenosine A2a receptor in macrophages," J. Immunol , 178:5921-29 (2007).
Hayes et al., "A Review of Modern Concepts of Healing of Cutaneous Wounds," J. Dermatol. Surg. Oncol. 3(2):188-93 (1977).
Hebert et al., "Transplantation of Kidneys from a Donor with Carbon Monoxide Poisoning," New Engl J Med 326(23):1571 (1992).

(56) References Cited

OTHER PUBLICATIONS

Horvath et al., "'Haemoxygenase-1 induction and exhaled markers of oxidative stress in lung diseases', summary of the ERS Research Seminar in Budapest, Hungary, Sep., 1999," Eur. Respir. J., 18(2):420-430, (2001).

Huizinga, Jan D., "Physiology and Pathophysiology of the Interstitial Cell of Cajal: From Bench to Bedside: II. Gastric motility: lessons from mutant mice on slow waves and innervation," Am. J. Physiol. 281:1129-1134, (2001).

Iberer et al., "Cardiac Allograft Harvesting after Carbon Monoxide Poisoning. Report of a Sucessful Orthotopic Heart Transplantation," *J Heart Lung Transplant* 12(3):499-500 (1993).

Johnson et al., "Relationships between drug activity in NCI preclinical in vitro and in vivo models and early clinical trials," Br. J. Cancer 84:1424-31 (2001).

Josko, "Vascular endothelial growth factor (VEGF) and its effect on angiogenesis," Medical Science Monitor 6:1047-52 (2000).

Kanoria, S. et al., "A model to study total hepatic ischemia-reperfusion injury," *Transplant Proc.*, 36(9):2586-2589 (2004).

Katori et al., "Heme Oxygenase-1 System in Organ Transplantation", *Transplantation* 74(7):905-912 (2002).

Kaufman et al., "Differential Roles of Mac-1$^+$ Cells, and CD4$^+$ and CD8$^+$ T Lymphocytes in Primary Nonfunction and Classic Rejection of Islet Allografts," *J Exp Med.* 172:291-302 (1990).

Ke et al., "Heme oxygenase 1 gene transfer prevents CD95/Fas ligand-mediated apoptosis and improves liver allograft survival via carbon monoxide signaling pathway," Hum. Gene Ther., 13:1189-99 (2002).

Kelly et al., "Traumatic shock induces type 2 nitric oxide synthase mRNA expression in the human liver," Surg. Forum, 47:32-33 (1996).

Koerner et al., "Extended Donor Criteria: Use of Cardiac Allografts after Carbon Monoxide Poisoning," *Transplantation* 63(9):1358-60 (1997).

Kozma et al, "Role of carbon monoxide in heme-induced vasodilation," Eur. J. Pharmacol., 323:R1-2 (1997).

Krause et al., "Recombinant human erythropoietin and VEGF have equal angiogenic potency: Investigation in a novel in vitro assay of human vascular tissues," European Heart J. 22:154 Abstract (2001).

Kyokane et al., "Carbon Monoxide From Heme Catabolism Protects Against Hepatobiliary Dysfunction in Endotoxin-Treated Rat Liver," Gastroenterology 120:1227-40 (2001).

Kyokane et al., "Gas Mediators and Organ Preservation. Roles of carbon monoxide in ameliorating hepatobiliary dysfunction in endotoxemic livers," Low Temp. Med., 27:12-17 (2001) (English abstract).

Lacy et al., "Transplantation of Pancreatic Islets," *Ann. Rev. Immunol* 2:183-98 (1984).

Laine et al., "Chronic rejection and late renal allograft dysfunction," Pediatr. Nephrol., 10:221-229 (1996).

Lee et al., "Intestinal Motility and Absorption in Acute Carbon Monoxide Poisoning," Seoul J. Med. 15:95-105 (1974); English translation.

Lee et al., "Regulation of Heme Oxygenase-1 Expression in Vivo and in Vitro in Hyperoxic Lung Injury", *Am. J. Respir. Cell Biol.* 14:556-568 (1996).

Lefer et al., "A Comparison of Vascular Biological Actions of Carbon Monoxide and Nitric Oxide", *Meth Find Exp Clin Pharmacol* 15(9):617-622 (1993).

Leikin et al., "The Toxic Patient as a Potential Organ Donor," *Am J Emerg Med* 12(2):151-4 (1994).

Libby and Pober, "Chronic Rejection," Immunity 14:387-97 (2001).

Liu et al., "Carbon monoxide and nitric oxide suppress the hypoxic induction of vascular endothelial growth factor gene via the 5' enhancer," J. Biol. Chem. 273(24):15257-62 (1998).

Mandrup-Poulsen et al., "Human Tumor Necrosis Factor Potentiates Human Interleukin 1-Mediated Rat Pancreatic β-Cell Cytotoxicity," *J. Immunol* 139:4077-82 (1987).

Mansouri et al., "Alteration of Platelet Aggregation by Cigarette Smoke and Carbon Monoxide," *Thromb Haemost* 48:286-8 (1982).

Maxwell et al., "Studies in Cancer Chemotherapy: XI. The Effect of CO, HCN, and Pituitrin Upon Tumor Growth", Dept. Of Cancer Research , Santa Barbara Cottage Hospital, pp. 270-282 (Jan. 30, 1933).

Mayr et al., "Effects of carbon monoxide inhalation during experimental endotoxemia in humans," Am. J. Respir. Crit. Care Med., 171:354-360 (2005).

Mazzola et al., "Carbon monoxide pretreatment prevents respiratory derangement and ameliorates hyperacute endotoxic shock in pigs," FASEB J. 19:2045-2047 (2005).

Medline Plus Medical Dictionary, definitions of organ, tissue and cell, accessed Oct. 9, 2007.

Meilin et al., Effects of carbon monoxide on the brain may be mediated by nitric oxide, *J Appl Physiol.* 81(3):1078-83 (1996).

Miller et al., "Heme oxygenase 2 is present in interstitial cell networks of the mouse small intestine," Gastroenterology 114:239-244 (1998).

Minamino et al., "Targeted expression of heme oxygenase-1 prevents the pulmonary inflammatory and vascular responses to hypoxia", *PNAS* 98(15):8798-8803 (2001).

Modification of Chronic Inflammation by Inhaled Carbon Monoxide in Patients With Stable Chronic Obstructive Pulmonary Disease (COPD), http://www.clinicaltrials.gov/ct/show/NCT00122694?order=1 (retrieved on Aug. 28, 2006).

Moore et al., "Carbon Monoxide Protects against Intestinal Dysmotility Associated with Small Bowel Transplantation," Gastroenterology 122:A38, (2002), Abstract.

Moore et al., "Carbon Monoxide Suppresses the Development of Ileus Associated with Surgical Manipulation of the Small Intestine," Gastroenterology 122:A61-A62, (2002), Abstract.

Moore et al., "Inhaled Carbon Monoxide Suppresses the Development of Postoperative Ileus in the Murine Small Intestine," Gastroenterology 124:377-91 (2003).

Moore et al., "Pre-treatment with Low Concentrations of Carbon Monoxide (250 to 75 ppm) for 3 hr prior to Laparotomy Protects Against Postoperative Ileus," Digestive Disease Week abstracts and Itinerary Planner 2003: Abstract No. M1337 (2003).

Mori et al., "Evaluation of hypothermic heart preservation with University of Wisconsin solution in heterotopically and orthotopically transplanted canine hearts," J. Heart Lung Transplant. 13:688-950 (1994).

Morse and Choi, "Heme oxygenase-1: from bench to bedside," Am. J. Respir. Crit. Care Med. 172:660-670 (2005).

Morse et al., "Carbon monoxide-dependent signaling," Crit. Care Med., 30:S12-S17, (2001).

Morse et al., "Suppression of inflammatory cytokine production by carbon monoxide involves the JNK pathway and AP-1," J. Biol. Chem., 278(39):36993-36998, (2003).

Motterlini et al., "Carbon Monoxide-Releasing Molecules: Characterization of Biochemical and Vascular Activities," Circ. Res. 90:e17-24 (2002).

Myers, "Cirrhotic cardiomyopathy and liver transplantation," *Liver Transpl* 6(4 Suppl 1):S44-52 (2000).

Nachar at al., "Low-Dose Inhaled Carbon Monoxide Reduces Pulmonary Vascular Resistance During Acute Hypoxemia in Adult Sheep," High Altitude Medicine & Biology 2:377-385 (2001).

Nagata et al. ,"Destruction of Islet Isografts by Severe Nonspecific Inflammation," *Transplant Proc.* 22:855-6 (1990).

Nakao et al., "A single intraperitoneal dose of carbon monoxide-saturated ringer's lactate solution ameliorates postoperative ileus in mice," J. Pharmacol. Exp. Ther. 319:1265-75 (2006).

Nakao et al., "Protective effect of carbon monoxide inhalation for cold-preserved small intestinal grafts," Surgery 134(2):285-292 (2003).

Nakao et al , "Immunomodulatory effects of inhaled carbon monoxide on rat syngeneic small bowel graft motility," Gut 52:1278-85 (2003).

Nakao et al., "Protective effect of carbon monoxide in transplantation," J. Cell. Mol. Med., 10:650-671 (2006).

Ning et al., "TGF-beta1 stimulates HO-1 via the p38 mitogen-activated protein kinase in A549 pulmonary epithelial cells," Am. J. Physiol. Lung Cell. Mol. Physiol., 283(5):L1094-L1102, (2002).

(56) References Cited

OTHER PUBLICATIONS

Okamoto, "Suppression of cytochrome P450 gene expression in the livers of mice with concavalin A-induced hepatitis," Eur. J. Pharmacol., 394:157-161 (2000).
Omaye, "Metabolic modulation of carbon monoxide toxicity," Toxicol. 180:139-150 (2002).
Otterbein et al., "Carbon monoxide suppresses arteriosclerotic lesions associated with chronic graft rejection and with balloon injury," Nature Medicine 9:183-90 (2003).
Otterbein et al., "Carbon monoxide at low concentrations induces growth arrest and modulates tumor growth in mice," Exp. Biol. Med., 228(5):633, (2003), Abstract.
Otterbein et al., "Carbon monoxide has anti-inflammatory effects involving the mitogen-activated protein kinase pathway", *Nature Medicine* 6(4): 422-8 (2000).
Otterbein et al., "Carbon Monoxide Inhibits TNFα-Induced Apoptosis and Cell Growth in Mouse Fibroblasts," American Journal of Respiratory and Critical Care Medicine 159(3 Suppl.):A285 (1999).
Otterbein et al., "Carbon Monoxide Mediates Anti-Inflammatory Effects via the P38 Mitogen Activated Protein Kinase Pathway," Acta Haematologica 103: 64, (2000), Abstract.
Otterbein et al., "Carbon Monoxide Modulates Lipolysaccaride (LPS)-Induced Inflammatory Responses in vivo and in vitro," American Journal of Respiratory and Critical Care Medicine 159(3 Suppl.):A481 (1999).
Otterbein et al., "Carbon Monoxide Protects Against Oxidant-Induced Lung Injury in Mice via the p38 Mitogen Activated Protein Kinase Pathway," Acta Haematologica 103:83, (2000), Abstrac.
Otterbein et al., "Carbon monoxide provides protection against hyperoxic lung injury", *The American Physiological Society* L688-L694 (1999).
Otterbein et al., "Carbon monoxide provides protection against hyperoxic lung injury in rats", *J Respiratory Critical Care Med* 159(3):A218 (1999).
Otterbein et al., "Carbon Monoxide, a Gaseous Molecule with Anti-Inflammatory Properties," pp. 133-156 in Disease Markers in Exhaled Breath, Marczin et al., eds., Marcel Dekker, Inc., New York, (2003).
Otterbein et al., "Exogenous administration of heme oxygenase-1 by gene transfer provides protection against hyperoxia-induced lung injury," J. Clin. Invest., 103(7):1047-1054, (1999).
Otterbein et al., "Heine oxygenase: colors of defense against cellular stress," Am. J. Physiol. Lung Cell. Mol. Physiol., 279(6):L1029-L1037, (2000).
Otterbein et al., "Mechanism of hemoglobin-induced protection against endotoxemia in rats: a ferritin-independent pathway", *Am J Physiol Lung Cell Mol Physiol* 272:L268-275 (1997).
Otterbein et al., "Protective effects of heme oxygenase-1 in acute lung injury," Chest. 116:61S-63S, (1999).
Otterbein LE, Choi AMK, "Carbon monoxide at low concentrations causes growth arrest and modulates tumor growth in mice,"[Abstract], Am. J. Respir. Crit. Care Med. 163:A476 (2001).
Otterbein, "Anti-Inflammatory Effects of Carbon Monoxide in the Lung," CRISP Data Base National Institute of Health; Doc. No. CRISP/2003HL071797-01A1, (2003).
Otterbein, "Carbon monoxide: innovative anti-inflammatory properties of an age-old gas molecule," Antioxid. Redox Signal., 4:309-319, (2002).
Pannen et al., "Protective Role of Endogenous Carbon Monoxide in Hepatic Microcirculatory Dysfunction after Hemorrhagic Shock in Rats," J. Clin. Invest. 102:1220-1228 (1998).
Paredi et al., "Increased Carbon Monoxide in Exhaled Air of Cystic Fibrosis Patients", *J Respiratory Critical Care Med* 159(3):A218 (1999).
Peek et al., "Extracorporeal Membrane Oxygenation for Adult Respiratory Failure," Chest 112(3)759-64 (1997).
Perrissoud et al., "Inhibiting or potentiating effects of flavonoids on carbon tetrachloride-induced toxicity in isolated rat hepatocytes," Arneimittelforschung, 36:1249-53 (1986).

Petrache et al., "Heme oxygenase-1 inhibits TNF-α-induced apoptosis in cultured fibroblasts," *Am. J. Physiol. Lung Cell Mol. Physiol*. 287: L312-L319 (2000).
Piantadosi et al., "Production of Hydroxyl Radical in the Hippocampus After CO Hypoxia Hypoxia in the Rat", *Free Radical Biol. & Med*. 22(4):725-732 (1997).
Pileggi et al., "Heme oxygenase-1 induction in islet cells results in protection from apoptosis and improved in vivo function after transplantation," Diabetes, 50(9):1983-1991, (2001).
Potter et al., "The inflammation-induced pathological chaperones ACT and apo-E are necessary catalysts of Alzheimer amyloid formation," Neurobiology of Aging 22:923-30 (2001).
Pozzoli et al., "Carbon Monoxide as a Novel Neuroendocrine Modulator: Inhibition of Stimulated Corticotropin-Releasing Hormone Release from Acute Rat Hypothalamic Explants," *Endocrinology* 135:2314-2317 (1994).
Rabinovitch et al., "Transfection of Human Pancreatic Islets With an Anti-Apoptotic Gene (bcl-2) Protects β-Cells From Cytokine-Induced Destruction," *Diabetes* 48:1223-9, 1999.
Ramakrishna et al., "Alterations in chemokine mRNA expression in animals receiving portal vein immunization and renal allo- or xenotransplantation precede altered cytokine production," J. Surg. Res., 87:62-72 (1999).
Raman et al., "Inhaled carbon monoxide inhibits intimal hyperplasia and provides added benefit with nitric oxide," J. Vasc. Surg. 44:151-158 (2006).
Ramlawi et al., "Inhaled Carbon Monoxide Prevents Graft-Induced Intimal Hyperplasia in Swine," J. Surg. Res. 138:121-127 (2007).
Rensing et al., "Differential expression pattern of heme oxygenase-1/heat shock protein 32 and nitric oxide synthase-II and their impact on liver injury in a rat model of hemorrhage and resuscitation," Crit. Care Med., 27:2766-75 (1999).
Ring et al., "The hepatic microvascular response to sepsis," Semin. Thromb. Hemost., 26:589-594 (2000).
Ringel et al., "Carbon Monoxide-induced Parkinsonism", J. neurol. Sci. 16:245-251 (1972).
Roberts et al., "Successful Heart Transplantation From a Victim of Carbon Monoxide Poisoning," *Ann Emerg Med* 26(5):652-5 (1995).
Ryter and Choi, "Heme Oxygenase-1: Molecular Mechanisms of Gene Expression in Oxygen-Related Stress," Antioxid. Redox Signal. 4:625-632, (2002).
Ryter et al., "Heme oxygenase/carbon monoxide signaling pathways: Regulation and functional significance," Mol. Cell. Biochem., 234-235(1-2):249-63, (2002).
Ryter et al., "Heme oxygenase-1/carbon monoxide: from basic science to therapeutic applications," Physiol. Rev. 86(2):583-650 (2006).
Ryter et al., "Mitogen Activated Protein Kinase (MAPK) Pathway Regulates Heme Oxygenase-1 Gene Expression by Hypoxia in Vascular Cells," Exp. Biol. Med., 228(5):607, (2003), Abstract.
Ryter et al., "Therapeutic applications of carbon monoxide in lung disease," Curr. Opin. Pharmacol., 6:257-262 (2006).
Sarady et al., "Carbon monoxide modulates endotoxin-induced production of granulocyte macrophage colony-stimulating factor in macrophages," Am. J. Respir. Cell. Mol. Biol., 27(6):739-745, (2002).
Sarady et al., "Cytoprotection by heme oxygenase/CO in the lung," in Disease Markers in Exhaled Breath, Marczin and Yacoub, eds., IOS Press, 346:73-78, (2002).
Sasidhar et al., "Exogenous Carbon Monoxide Attenuates Mitogen Activated Protein Kinase (MAPK) Activation in Rat Pulmonary Artery Endothelial Cells Exposed to Hypoxia," American Journal of Respiratory and Critical Care Medicine. 1999;159(3 Suppl.):A352.
Sass et al., "Heme Oxygenase-1 Induction Prevents Apoptotic Liver Damage in Mice," Naunyn-Schmiedeberg's Archives of Pharmacology 367:R78, (2003).
Sato et al., "Carbon monoxide can fully substitute Heme Oxygenase-1 in suppressing the rejection of mouse to rat cardiac transplants," Acta Haematologica, 103(Suppl. 1):87, Abstract 348 (2000).
Sato et al., "Heme oxygenase-1 or carbon monoxide prevents the inflammatory response associated with xenograft rejection," Acta Haematologica, 103(Suppl. 1):87, Abstract 345 (2000).

(56) References Cited

OTHER PUBLICATIONS

Sato et al., "Carbon Monoxide Generated by Heme Oxygenase-1 Suppresses the Rejection of Mouse-to-Rat Cardiac Transplants," *J. Immunol.* 166: 4185-4194 (2001).
Schipper et al., "Expression of Heme Oxygenase-1 in the Senescent and Alzheimer-diseased Brain", *Annals of Neurology* 37(6): 758-68 (1995).
Sethi et al, "Differential modulation by exogenous carbon monoxide of TNF-alpha stimulated mitogen-activated protein kinases in rat pulmonary artery endothelial cells," Antioxid. Redox Signal., 4:241-8, (2002).
Sethi et al., "Differential Effects of Exogenous Carbon Monoxide on TNF-α-Induced Mitogen Activated Protein (MAP) Kinase Signaling Pathway in Rat Pulmonary Artery Endothelial Cells," American Journal of Respiratory and Critical Care Medicine 159(3 Suppl.):A350 (1999).
Seyfried et al., "HO-1 induction protects mice from Immune-mediated liver injury," Naunyn-Schmiedeberg's Archives of Pharmacology 367:R80 (2003).
Shahin et al., "Carboxyhemoglobin in pediatric sepsis and the systematic inflammatory response syndrome," Clinical Intensive Care 11(6):311-17 (2000).
Shapiro et al., "Islet Transplantation in Seven Patients with Type 1 Diabetes Mellitus Using a Glucocorticoid-Free Immunosuppressive Regimen," *N Engl. J. Med.*, 343:230-8, 2000.
Shennib et al., "Successful transplantation of a lung allograft from a carbon monoxide-poisoning victim," *Heart Lung Transplant* 11(1 Pt 1): 68-71 (1992).
Singhal et al., "Effects of Normobaric Hyperoxia in a Rat Model of Focal Cerebral Ischemia-Reperfusion", *J Cerebral Blood Flow & Medicine* 22:861-868 (2002).
Siow et al., "Heme oxygenase-carbon monoxide signalling pathway in atherosclerosis: anti-atherogenic actions of bilirubin and carbon monoxide?", *Cardiovascular Research* 41:385-394 (1999).
Slebos et al., "Heme oxygenase-1 and carbon monoxide in pulmonary medicine," Respir Res. 4(7):1-13, (2003).
Smith et al., "Successful Heart Transplantation with Cardiac Allografts Exposed to Carbon Monoxide Poisoning," *Heart Lung Transplant* 11(4 Pt. 1):698-700 (1992).
Soares et al, "Heme oxygenase-1, a protective gene that prevents the rejection of transplanted organs," Immunol Rev. 184:275-85, (2001).
Soares et al, "Modulation of endothelial cell apoptosis by heme oxygenase-1-derived carbon monoxide," Antioxid. Redox Signal., 4:321-329, (2002).
Soares et al., "Expression of heme oxygenase-1 can determine cardiac xenograft survival," *Nat Med.* 4(9):1073-1077 (1998).
Soares et al., "Heme Oxygenase-1 and/or Carbon Monoxide can Promote Organ Graft Survival," in Disease Markers in Exhaled Breath, Marczin and Yacoub, eds., IOS Press, 346:267-273, (2002).
Soares et al., "Heme oxygenase-1: from biology to therapeutic potential," Trends Mol. Med., 15:50-56 (2009).
Song et al., "Carbon monoxide induces cytoprotection in rat orthotopic lung transplantation via anti-inflammatory and anti-apoptotic effects," Am. J. Pathol., 163(1):231-242, (2003).
Song et al., "Carbon monoxide inhibits human airway smooth muscle cell proliferation via mitogen-activated protein kinase pathway," Am. J. Respir. Cell. Mol. Biol. 27(5):603-610, (2002).
Song et al., "Regulation of IL-1beta-induced GM-CSF production in human airway smooth muscle cells by carbon monoxide," Am. J. Physiol. Lung Cell. Mol. Physiol., 284(1):L50-L56, (2003).
Stephens et al., "Further Observations Regarding Carbon Monoxide Gas as an Important Factor in the Causation of Industrial Cancer", *Medical Press and Circular* 183:283-288 (1933).
Stewart, "The effect of carbon monoxide on humans," J. Occup. Med. 18:304-309 (1976).
Stewart, "The effects of low concentrations of carbon monoxide in man," Scand. J. Respir. Dis. Suppl. 91:56-62 (1974).

STN online, file BIOSIS, Acc. No. 1997:153343, Doc. No. PREV199799452546 (Scheuer, Histopathology (Oxford) (1997), 30(2):103-105) Abstract.
STN online, file BIOTECHNO, Acc. No. 1995:25320080 (Boermeester et al., Hepatology (1995), 22(5):1499-1506) Abstract.
STN online, file EMBASE, Acc. No. 0048114152 (Lundquist et al., Annals of Clinical Research (1970), 2(3):197-203) Abstract.
STN online, file MEDLINE, Acc. No. 1995032316, Doc. No. 7945565 (Adams, Alcohol and Alcoholism (Oxford, Oxfordshire) (1994), 29(3):249-260) Abstract.
STN online, file MEDLINE, Acc. No. 87049029 (Perrissoud et al., Arzneimittel-Forschung, 36(8):1249-1253 (1986)).
Stupfel and Bouley, "Physiological and Biochemical Effects on Rats and Mice Exposed to Small Concentrations of Carbon Monoxide for Long Periods," Ann. N.Y. Acad. Sci. 174:343-368 (1970).
Suganuma et al., "A new process of cancer prevention mediated through inhibition of tumor necrosis factor alpha expression," Cancer Res. 56(16):3711-5 (1996).
Tamayo et al., "Carbon monoxide inhibits hypoxic pulmonary vasoconstriction in rats by a cGMP-independent mechanism", *Pflugers Arch.* 434(6):698-704 (1997).
Taylor, "Anti-TNF Therapy for Rheumatoid Arthritis and Other Inflammatory Diseases", *Molecular Biotechnology* 19:153-168 (2001).
Tenderich et al., "Hemodynamic follow-up of cardiac allografts from poisoned donors," *Transplantation* 66(9):1163-7 (1998).
Tenhunen et al., "The Enzymatic Conversion of Heme to Bilirubin by Microsomal Heme Oxygenase," *Proc Natl Acad Sci USA* 61:748-755 (1968).
The Merck Manual (16$^{th}$ Ed. 1992) pp. 646-657.
The New Encyclopedia Britannica (15$^{th}$ ed. 1994) vol. 26, *Macropaedia*, p. 756.
Thiemermann "Inhaled CO: deadly gas or novel therapeutic?" Nature Medicine 7(5): 534-35 (2001).
Thom et al, "'Therapeutic' Carbon Monoxide May Be Toxic," Am. J. Respir. Crit. Care Med., 171(11):1318 (2005).
Thornton et al., "Cytokine-Induced Gene Expression of a Neutrophil Chemotatic Factor/IL-8 in Human Hepatocytes," The Journal of Immunology, 144(7):2609-2613 (1990).
Tobiasch et al, "Heme oxygenase-1 protects pancreatic β cells from apoptosis caused by various stimuli," J. Investig. Med., 49:566-71, (2001).
Toda et al., "Exogenous carbon monoxide protects endothelial cells against oxidant stress and improves graft function after lung transplantation," Circulation, 98(17):I265 (1998).
Tulis et al., "Adenovirus-Mediated Heme Oxygenase-1 Gene Delivery Inhibits Injury-Induced Vascular Neointima Formation", *Circulation* 104:2710-2715 (2001).
Utz et al., "Carbon Monoxide Relaxes Ileal Smooth Muscle Through Activation of Guanylate Cyclase," *Biochem Pharmacol.* 47:1195-201, 1991.
Vassalli et al., "Inhibition of Hypoxic Pulmonary Vasoconstriction by Carbon Monoxide in Dogs", European Respiratory Journal, ERS Annual Congress, Geneva, Switzerland, Sep. 19-23, 1998.
Verma et al., "Carbon Monoxide: A Putative Neural Messenger," *Science* 259:381-384, 1993.
Verran et al., "Use of Liver Allografts from Carbon Monoxide Poisoned Cadaveric Donors," *Transplantation* 62(10):1514-5 (1996).
Vreman et al., "Carbon monoxide and carboxyhemoglobin," Adv. Pediatr. 42:303-34 (1995).
Wang et al., "Carbon monoxide-induced vasorelaxation and the underlying mechanisms," Br. J. Pharmacol. 121:927-934 (1997).
Wang et al., "Resurgence of carbon monoxide: an endogenous gaseous vasorelaxing factor", Can. J. Physiol. Pharmacol. 76:1-15 (1998).
Weir et al., "Islet transplantation as a treatment for diabetes," *J. Am. Optom. Assoc.* 69:727-32, 2000.
Weir et al., "Scientific and Political Impediments to Successful Islet Transplantation," *Diabetes* 46:1247-56, 1997.
Welty et al., "Hyperoxic Lung Injury is Potentiated by SPC-Promotor Driven Expression of an HO-1 Transgene in Mice", *J Respiratory Critical Care Med* 159(3):A218 (1999).

(56) References Cited

OTHER PUBLICATIONS

Weng et al., "Transpulmonary HO-1 Gene Delivery in Neonatal Mice", *J Respiratory Critical Care Med* 59(3):A218 (1999).
Wing-Gaia et al., International Journal of Sport Nutrition and Exercise Metabolism, 15:680-688 (2005).
Wright and Shephard, "Physiological effects of carbon monoxide," Int. Rev. Physiol. 20:311-68 (1979).
Yamashita et al., "Effects of HO-1 induction and carbon monoxide on cardiac transplantation in mice," Exp. Biol. Med., 228(5):616, (2003), Abstract.
Yuan et al., "Evidence of increased endogenous carbon monoxide production in newborn rat endotoxicosis," *Chinese Medical Sciences Journal* (1997), vol. 12, No. 4, 212-215.
Zegdi et al., "Increased endogenous carbon monoxide production in severe sepsis," Intensive Care Medicine 23:793-96 (2002).
Zhang et al., "Carbon monoxide inhibition of apoptosis during ischemia-reperfusion lung injury is dependent on the p38 mitogen-activated protein kinase pathway and involves caspase 3," J. Biol. Chem., 278(2):1248-1258, (2003).
Zhang et al., "Mitogen-activated protein kinases regulate HO-1 gene transcription after ischemia-reperfusion lung injury," Am. J. Physiol. Lung Cell. Mol. Physiol., 283(4):L815-L829, (2002).
Zhou et al., "Endogenous carbon monoxide and acute lung injury," Section of Respiratory System Foreign Medical Sciences 19:185-187 (1999) (English translation provided).
Zuckerbraun and Billiar, "Heine oxygenase-1: a cellular Hercules" Hepatology, 37(4):742-744, (2003).
Zuckerbraun et al., "Carbon monoxide attenuated the development of necrotizing enterocolitis in an animal model," Surgical Infection Society 3:83 (2002).
Zuckerbraun et al., "Carbon monoxide inhibits intestinal inducible nitric oxide synthase production and ameliorates intestinal inflammation in experimental NEC," J. Amer. College of Surgeons 197:S50 (2003).
Zuckerbraun et al., "Carbon Monoxide Protects against Liver Failure through Nitric Oxide-induced Heme Oxygenase 1," J. Exp. Med. 198:1707-716 (2003).
Zuckerbraun et al., "Carbon Monoxide Protects Hepatocytes from TNF-alpha/Actinomycin D Induced Cell Death," Critical Care Medicine 29:A59 (2001).
Remington's Pharmaceutical Sciences, pp. 1787-1789, 1985.
Australian Office Action; Application No. 2003234585; mailed Feb. 22, 2007; Applicants: Yale University and University of Pittsburgh System of the Commonwealth of Higher Education; 3 pages.
Australian Office Action; Application No. 2003234585; mailed Oct. 3, 2008; Applicants: Yale University and University of Pittsburgh System of the Commonwealth of Higher Education; 1 page.
Canadian Office Action; Application No. 2,485,465; mailed Oct. 22, 2009; Applicants: Yale University and University of Pittsburgh System of the Commonwealth of Higher Education; 3 pages.
Chinese Office Action; Application No. 03816323.3; issued Sep. 26, 2006; Applicants: Yale University and University of Pittsburgh System of the Commonwealth of Higher Education; 6 pages.
Chinese Office Action; Application No. 03816323.3; issued Apr. 3, 2009; Applicants: Yale University and University of Pittsburgh System of the Commonwealth of Higher Education; 3 pages.
Chinese Office Action; Application No. 03816323.3; issued Jul. 24, 2009; Applicants: Yale University and University of Pittsburgh System of the Commonwealth of Higher Education; 4 pages.
Indian Office Action; Application No. 3596/DELNP/2004; mailed Aug. 3, 2010; Applicant: Yale University; 2 pages.
Japanese Office Action; Application No. 2004-504976; Applicant: Yale University et al., mailed Nov. 5, 2009; 5 pages.
Mexican Office Action; Application No. PA/a/2004/011426; mailed Aug. 15, 2007; Applicants: Yale University and University of Pittsburgh System of the Commonwealth of Higher Education; 2 pages.
Mexican Office Action; Application No. MX/a/2008/001255; mailed Nov. 3, 2011; Applicants: Yale University and University of Pittsburgh System of the Commonwealth of Higher Education; 5 pages.
USPTO Final Office Action in U.S. App. No. 10/676,280, mailed Apr. 16, 2009, 17 pages.
USPTO Notice of Allowance in U.S. Appl. No. 10/371,666, mailed Oct. 20, 2009, 15 pages.
USPTO Notice of Allowance in U.S. Appl. No. 10/053,535, mailed Oct. 21, 2009, 20 pages.
USPTO Non-Final Office Action in U.S. Appl. No. 10/600,182, mailed Apr. 30, 2009, 10 pages.
USPTO Non-Final Office Action in U.S. Appl. No. 13/544,701, mailed Sep. 28, 2012, 31 pages.
USPTO Non-Final Office Action in U.S. Appl. No. 10/439,632, mailed Apr. 20, 2005, 11 pages.
Fish & Richardson P.C. Response to Office Action in U.S. Appl. No. 10/439,632, of Apr. 20, 2005, filed on Jul. 20, 2005, 3 pages.
USPTO Final Office Action in U.S. Appl. No. 10/439,632, mailed Oct. 17, 2005, 6 pages.
Fish & Richardson P.C. Notice of Appeal in U.S. Appl. No. 10/439,632, filed on Apr. 14, 2006, 1 page.
Fish & Richardson P.C. Request for Continued Examination in U.S. Appl. No. 10/439,632, filed on Sep. 14, 2006, 158 pages.
USPTO Non-Final Office Action in U.S. Appl. No. 10/439,632, mailed Dec. 11, 2006, 20 pages.
Fish & Richardson P.C. Response to Office Action in U.S. Appl. No. 10/439,632, of Dec. 11, 2006, filed on Jun. 11, 2007, 52 pages.
USPTO Non-Final Office Action in U.S. Appl. No. 10/439,632, mailed Jun. 3, 2008, 18 pages.
Fish & Richardson P.C. Response to Office Action in U.S. Appl. No. 10/439,632, of Dec. 11, 2006, filed on Oct. 3, 2008, 36 pages.
USPTO Final Office Action in U.S. Appl. No. 10/439,632, mailed Aug. 6, 2009, 9 pages.
Fish & Richardson P.C. Request for Continued Examination in U.S. Appl. No. 10/439,632, filed on Nov. 13, 2009, 6 pages.
Fish & Richardson P.C. Supplement Amendment in U.S. Appl. No. 10/439,632, filed on Nov. 19, 2009, 5 pages.
USPTO Non Final Office Action in U.S. Appl. No. 10/439,632, mailed Feb. 5, 2010, 13 pages.
Fish & Richardson P.C. Response to Office Action in U.S. Appl. No. 10/439,632, of Feb. 5, 2010, filed on Jun. 7, 2010, 20 pages.
USPTO Final Office Action in U.S. Appl. No. 10/439,632, mailed Aug. 16, 2010, 11 pages.
Fish & Richardson P.C. Request for Continued Examination in U.S. Appl. No. 10/439,632, filed Dec. 16, 2010, 13 pages.
USPTO Non Final Office Action in U.S. Appl. No. 10/439,632, mailed Apr. 21, 2011, 11 pages.
Fish & Richardson P.C. Response to Office Action in U.S. Appl. No. 10/439,632, of Apr. 21, 2011, filed on Jun. 20, 2011, 20 pages.
USPTO Final Office Action in U.S. Appl. No. 10/439,632, mailed Jan. 11, 2012, 11 pages.

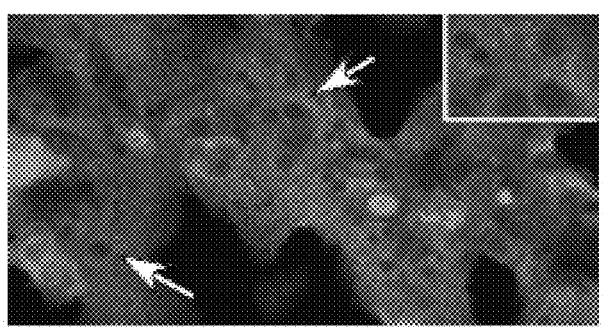
FIG. 6A  Air
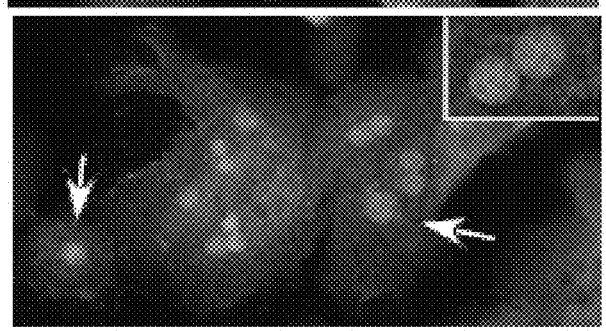
FIG. 6B  Cytokine Mixture
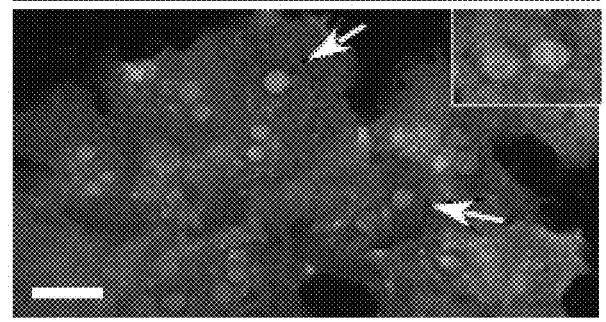
FIG. 6C  CO 250ppm FIG. 13A
FIG. 13B
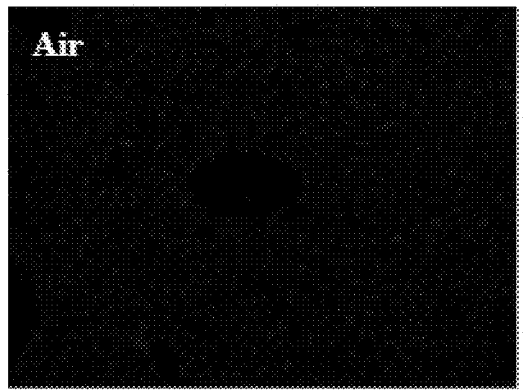
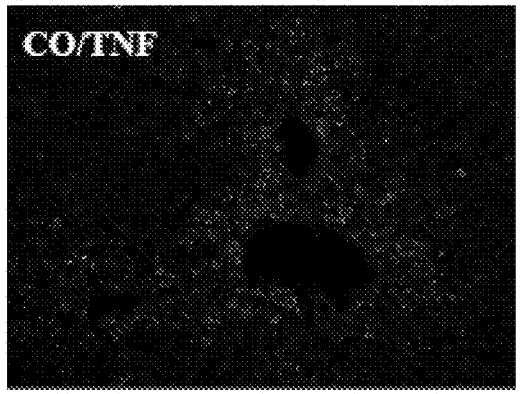
FIG. 13C
FIG. 13D

SEQUENCE LISTING

<160> NUMBER OF SEQ ID NOS: 1

<210> SEQ ID NO 1
<211> LENGTH: 12
<212> TYPE: DNA
<213> ORGANISM: Artificial Sequence
<220> FEATURE:
<223> OTHER INFORMATION: laboratory-constructed sequence

<400> SEQUENCE: 1
ggggactttc cc                                                           12

METHODS OF TREATING HEPATITIS

CROSS-REFERENCE TO RELATED APPLICATIONS

This application is a continuation of U.S. application Ser. No. 13/803,330, filed Mar. 14, 2013, which is a continuation of U.S. application Ser. No. 13/544,701, filed Jul. 9, 2012, which is a continuation of U.S. application Ser. No. 10/439,632, filed May 16, 2003, which claims priority to U.S. Provisional Application No. 60/381,527 filed May 17, 2002, each of which is incorporated herein by reference in its entirety.

STATEMENT AS TO FEDERALLY SPONSORED RESEARCH

This invention was made with U.S. Government support under National Institutes of Health Grant Nos. R01-GM-44100, HL 58688, HL55330, HL60234, and AI42365. The Government has certain rights in this invention.

TECHNICAL FIELD

This invention relates to the treatment of hepatitis.

BACKGROUND

Carbon monoxide gas is poisonous in high concentrations. However, it is now recognized as an important signaling molecule (Verma et al., Science 259:381-384, 1993). It has also been suggested that carbon monoxide acts as a neuronal messenger molecule in the brain (Id.) and as a neuro-endocrine modulator in the hypothalamus (Pozzoli et al., Endocrinology 735:2314-2317, 1994). Like nitric oxide (NO), carbon monoxide is a smooth muscle relaxant (Utz et al., Biochem Pharmacol. 47:195-201, 1991; Christodoulides et al., Circulation 97:2306-9, 1995) and inhibits platelet aggregation (Mansouri et al., Thromb Haemost. 48:286-8, 1982). Inhalation of low levels of carbon monoxide (CO) has been shown to have anti-inflammatory effects in some models.

Hepatitis is a disease characterized by inflammation of the liver. The inflammation can be characterized by diffuse or patchy necrosis affecting acini. Causative agents of hepatitis include, for example, viruses, e.g., specific hepatitis viruses, e.g., hepatitis A, B, C, D, E, and G viruses; alcohol; and other drugs (e.g., isoniazid, methyldopa, acetaminophen, amiodarone, and nitrofurantoin) (see *The Merck Manual of Diagnosis and Therapy*, 17th Edition, Section 4, Chapter 42).

SUMMARY

The present invention is based, in part, on the discovery that administration of CO can protect against the development of hepatitis.

Accordingly, the present invention features a method of treating, preventing, or reducing the risk of, hepatitis in a patient. The method includes identifying a patient diagnosed as suffering from or at risk for hepatitis (e.g., a patient diagnosed as suffering from or at risk for hepatitis), and administering to the patient a pharmaceutical composition comprising an amount of carbon monoxide effective to treat hepatitis in the patient.

The pharmaceutical composition can be administered to the patient by any method known in the art for administering gases and/or liquids to patients, e.g., via inhalation, insufflation, infusion, injection, and/or ingestion. In one embodiment of the present invention, the pharmaceutical composition is administered to the patient by inhalation. In another embodiment, the pharmaceutical composition is administered to the patient orally. In still another embodiment, the pharmaceutical composition is administered directly to the abdominal cavity of the patient. In yet another embodiment, the pharmaceutical composition is administered by an extracorporeal membrane gas exchange device or an artificial lung. In another embodiment, the patient is an alcoholic.

The patient can be an animal, human or non-human. For example, the patient can be any mammal, e.g., humans, other primates, pigs, rodents such as mice and rats, rabbits, guinea pigs, hamsters, cows, horses, cats, dogs, sheep and goats. The hepatitis can be the result of, or a person may be considered at risk for hepatitis because of, any of a number of factors, e.g., infections, e.g., viral infections, e.g., infection with hepatitis A, B, C, D, E and/or G virus; alcohol use (e.g., alcoholism); drug use (e.g., one or more drugs described herein, e.g., acetaminophen, anesthetics, antituberculous drugs, antifungal agents, antidiabetic drugs, neuroleptic agents, and drugs used to treat HIV infection and AIDS); autoimmune conditions (e.g., autoimmune hepatitis); and/or surgical procedures. The pharmaceutical composition can be in any form, e.g., gaseous or liquid form.

In another embodiment, the method further includes administering to the patient at least one of the following treatments: inducing HO-1 or ferritin in the patient; expressing recombinant HO-1 or ferritin in the patient; and administering a pharmaceutical composition comprising HO-1, bilirubin, biliverdin, ferritin, or apoferritin, iron, desferoxamine, or iron dextran to the patient. Also contemplated is use of CO and any of the above-listed agents in the preparation of a medicament for treatment or prevention of hepatitis.

In another embodiment, the hepatitis (or the risk for hepatitis) is not caused by surgery (e.g., abdominal or transplant surgery), bacterial endotoxin, septic shock, and/or systemic inflammation.

In another aspect, the invention features a method of treating or preventing hepatitis in a patient, which includes identifying a patient suffering from or at risk for hepatitis (e.g., a patient diagnosed as suffering from or at risk for hepatitis), providing a vessel containing a pressurized gas comprising carbon monoxide gas, releasing the pressurized gas from the vessel to form an atmosphere comprising carbon monoxide gas, and exposing the patient to the atmosphere, wherein the amount of carbon monoxide in the atmosphere is sufficient to treat hepatitis in the patient.

In still another aspect, the invention features a method of performing abdominal surgery, e.g., liver transplantation, on a patient, which includes identifying a patient in need of abdominal surgery, wherein hepatitis is a risk of the abdominal surgery; performing abdominal surgery on the patient, and before, during, or after the performing step, causing the patient to inhale an amount of carbon monoxide gas sufficient to reduce the risk of hepatitis in the patient. Also contemplated is use of CO in the preparation of a medicament, e.g., a gaseous or liquid medicament, for use in the treatment or prevention of hepatitis.

The invention also features a method of treating hepatitis in a patient suffering from or at risk for hepatitis not caused by surgery and/or endotoxin, e.g., hepatitis caused by any factor described herein other than surgery and/or endotoxin. The method includes identifying a patient suffering from or at risk for hepatitis not caused by surgery and/or endotoxin and administering to the patient a pharmaceutical composition comprising an amount of carbon monoxide effective to treat hepatitis in the patient.

Also within the invention is a method of administering a hepatitis-inducing drug (i.e., a hepatotoxic drug, e.g., isoniazid, methyldopa, acetaminophen, amiodarone, or nitrofurantoin) to a patient. The method includes administering the drug to the patient, and before, during, and/or after administering the drug, administering to the patient a pharmaceutical composition comprising carbon monoxide in an amount effective to treat hepatitis in the patient.

In another aspect, the invention provides a vessel comprising medical grade compressed CO gas. The vessel can bear a label indicating that the gas can be used to treat hepatitis in a patient. Alternatively or in addition, the vessel can bear a label indicating that the gas can be administered to a patient in conjunction with administration of a hepatitis-inducing drug (i.e., a hepatotoxic drug), e.g., acetaminophen. The CO gas can be in an admixture with nitrogen gas, with nitric oxide and nitrogen gas, or with an oxygen-containing gas. The CO gas can be present in the admixture at a concentration of at least about 0.025%, e.g., at least about 0.05%, 0.10%, 0.50%, 1.0%, 2.0%, 10%, 50%, or 90%.

Also within the invention is the use of CO in the manufacture of a medicament for treatment or prevention of hepatitis. The medicament can be used in a method for treating hepatitis in a patient suffering from or at risk for hepatitis in accordance with the methods described herein. The medicament can be in any form described herein, e.g., a liquid or gaseous CO composition.

Unless otherwise defined, all technical and scientific terms used herein have the same meaning as commonly understood by one of ordinary skill in the art to which this invention belongs. Suitable methods and materials are described below, although methods and materials similar or equivalent to those described herein can be used in the practice or testing of the present invention. All publications, patent applications, patents, and other references mentioned herein are incorporated by reference in their entirety. In case of conflict, the present specification, including definitions, will control. The materials, methods, and examples are illustrative only and not intended to be limiting.

The details of one or more embodiments of the invention are set forth in the description below. Other features, objects, and advantages of the invention will be apparent from the description and the claims.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 6A-6C are photomicrographs of primary hepatocytes immunostained to detect nuclear p65 localization, illustrating that exogenous CO causes an increase in NF-κB activation in hepatocytes. FIG. 6A: air-exposed hepatocytes. FIG. 6B: hepatocytes exposed to cytokine mixture (TNF-α (500 U/ml), IL-1β (100 U/ml), and IFN-δ (100 U/ml)). FIG. 6C: CO-exposed hepatocytes. Images are representative of 6 different fields. Bar represents 10 μm.

FIGS. 11A and 11B: liver samples from mice exposed to room air and CO, respectively, and stained with hematoxylin & eosin (H & E). FIGS. 11C and 11D: liver samples from TNF-α/D-Gal-treated mice exposed to room air and CO, respectively, and stained with H & E. FIGS. 11E and 11F: liver samples from TNF-α/D-Gal-treated mice exposed to room air and CO, respectively, and stained to detect activated caspase-3. FIGS. 11G and 11H: liver samples from TNF-α/D-Gal-treated mice exposed to room air and CO, respectively, and stained using terminal deoxynucleotidyl transferase mediated dUTP nick end labeling (TUNEL). Images are representative sections from 15-20 sections/liver from 3-4 individual mice/group. Bar represents 20 μm.

FIGS. 13A-13D are photomicrographs of liver samples illustrating that the livers of mice exposed to TNF-α/D-Gal and treated with inhaled CO display increased iNOS protein levels. FIG. 13A: liver sample from room air-exposed mouse. FIG. 13B: liver sample from CO-exposed mouse. FIG. 13C: liver sample from mouse exposed to TNF-α/D-Gal and room air. FIG. 13D: liver sample from mouse exposed to TNF-α/D-Gal and CO. Images are representative of 6 separate animals and 6-10 different sections/liver sample. Bar represents 20 μm.

DETAILED DESCRIPTION

Figure 1:
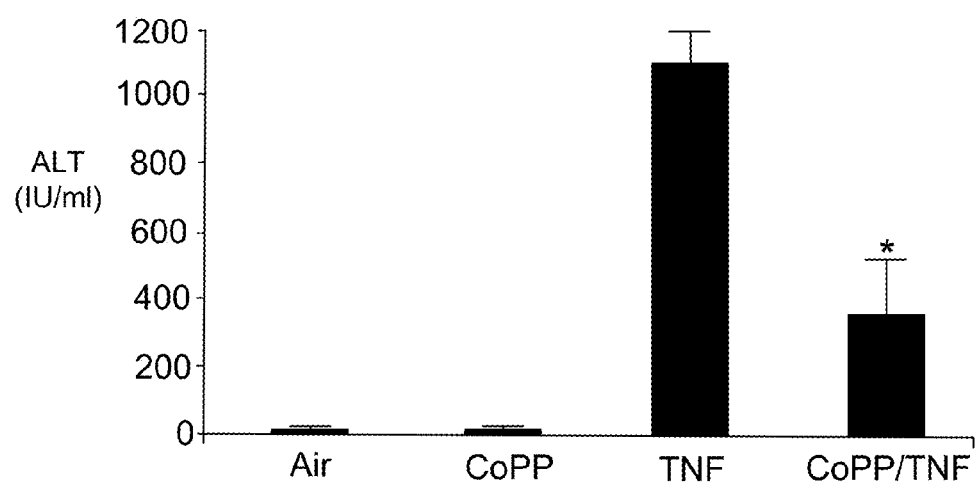
FIG. 1 is a bar graph illustrating that induction of HO-1 protects mouse hepatocytes from TNF-α/D-gal-induced cell death. CoPP=cobalt protoporphyrin; ALT=serum alanine aminotransferase; TNF=tumor necrosis factor alpha. Results are the mean±SD of 6-8 mice/group *p<0.005.

The term "carbon monoxide" (or "CO") as used herein describes molecular carbon monoxide in its gaseous state, compressed into liquid form, or dissolved in aqueous solution. The terms "carbon monoxide composition" and "pharmaceutical composition comprising carbon monoxide" is used throughout the specification to describe a gaseous or liquid composition containing carbon monoxide that can be administered to a patient and/or an organ, e.g., the liver. The skilled practitioner will recognize which form of the pharmaceutical composition, e.g., gaseous, liquid, or both gaseous and liquid forms, is preferred for a given application.

The terms "effective amount" and "effective to treat," as used herein, refer to an amount or concentration of carbon monoxide utilized for period of time (including acute or chronic administration and periodic or continuous administration) that is effective within the context of its administration for causing an intended effect or physiological outcome. Effective amounts of carbon monoxide for use in the present invention include, for example, amounts that prevent hepatitis, reduce the risk of hepatitis, reduce the symptoms of hepatitis, or improve the outcome of other hepatitis treatments.

For gases, effective amounts of carbon monoxide generally fall within the range of about 0.0000001% to about 0.3% by weight, e.g., 0.0001% to about 0.25% by weight, preferably at least about 0.001%, e.g., at least 0.005%, 0.010%, 0.02%, 0.025%, 0.03%, 0.04%, 0.05%, 0.06%, 0.08%, 0.10%, 0.15%, 0.20%, 0.22%, or 0.24% by weight carbon monoxide. Preferred ranges include, e.g., 0.001% to about 0.24%, about 0.005% to about 0.22%, about 0.005% to about 0.05%, about 0.010% to about 0.20%, about 0.02% to about 0.15%, about 0.025% to about 0.10%, or about 0.03% to about 0.08%, or about 0.04% to about 0.06%. For liquid solutions of CO, effective amounts generally fall within the range of about 0.0001 to about 0.0044 g CO/100 g liquid, e.g., at least 0.0001, 0.0002, 0.0004, 0.0006, 0.0008, 0.0010, 0.0013, 0.0014, 0.0015, 0.0016, 0.0018, 0.0020, 0.0021, 0.0022, 0.0024, 0.0026, 0.0028, 0.0030, 0.0032, 0.0035, 0.0037, 0.0040, or 0.0042 g CO/100 g aqueous solution. Preferred ranges include, e.g., about 0.0010 to about 0.0030 g CO/100 g liquid, about 0.0015 to about 0.0026 g CO/100 g liquid, or about 0.0018 to about 0.0024 g CO/100 g liquid. A skilled practitioner will appreciate that amounts outside of these ranges may be used, depending upon the application.

The term "patient" is used throughout the specification to describe an animal, human or non-human, to whom treatment according to the methods of the present invention is provided. Veterinary applications are contemplated by the present invention. The term includes but is not limited to mammals, e.g., humans, other primates, pigs, rodents such as mice and rats, rabbits, guinea pigs, hamsters, cows, horses, cats, dogs, sheep and goats. The term "treat(ment)," is used herein to describe delaying the onset of, inhibiting, or alleviating the effects of a condition, e.g., hepatitis, in a patient.

The term "hepatitis" is an art-recognized term and is used herein to refer to a disease of patients characterized in part by inflammation of the liver. Causative agents of hepatitis include, for example, infections, e.g., infection with specific hepatitis viruses, e.g., hepatitis A, B, C, D, E, and G viruses; or hepatotoxic agents, e.g., hepatotoxic drugs (e.g., isoniazid, methyldopa, acetaminophen, amiodarone, and nitrofurantoin), and toxins (e.g., endotoxin or environmental toxins). Hepatitis may occur postoperatively in liver transplantation patients. Further examples of drugs and toxins that may cause hepatitis (i.e., hepatotoxic agents) are described in Feldman: Sleisenger & Fordtran's Gastrointestinal and Liver Disease, 7th ed., Chapter 17 (Liver Disease Caused by Drugs, Anesthetics, and Toxins), the contents of which are expressly incorporated herein by reference in their entirety. Such examples include, but are not limited to, methyldopa and phenyloin, barbiturates, e.g., phenobarbital; sulfonamides (e.g., in combination drugs such as co-trimoxazole (sulfamethoxazole and trimethoprim); sulfasalazine; salicylates; disulfuram; β-adrenergic blocking agents e.g., acebutolol, labetalol, and metoprolol); calcium channel blockers, e.g., nifedipine, verapamil, and diltiazem; synthetic retinoids, e.g., etretinate; gastric acid suppression drugs e.g., oxmetidine, ebrotidine, cimetidine, ranitidine, omeprazole and famotidine; leukotriene receptor antagonists, e.g., zafirlukast; anti-tuberculous drugs, e.g., rifampicin and pyrazinamide; antifungal agents, e.g., ketoconazole, terbinafine, fluconazole, and itraconazole; antidiabetic drugs, e.g., thiazolidinediones, e.g., troglitazone and rosiglitazone; drugs used in neurologic disorders, e.g., neuroleptic agents, antidepressants (e.g., fluoxetine, paroxetine, venlafaxine, trazodone, tolcapone, and nefazodone), hypnotics (e.g., alpidem, zolpidem, and bentazepam), and other drugs, e.g., tacrine, dantrolene, riluzole, tizanidine, and alverine; nonsteroidal anti-inflammatory drugs, e.g., bromfenac; COX-2 inhibitors; cyproterone acetate; leflunomide; antiviral agents, e.g., fialuridine, didanosine, zalcitabine, stavudine, lamivudine, zidovudine, abacavir; anticancer drugs, e.g., tamoxifen and methotrexate; recreational drugs, e.g., cocaine, phencyclidine, and 5-methoxy-3,4-methylenedioxymethamphetamine; L-asparaginase; amodiaquine; hycanthone; anesthetic agents; e.g., halothane, enflurane, and isoflurane; vitamins e.g., vitamin A; and dietary and/or environmental toxins, e.g., pyrrolizidine alkaloids, toxin from *Amanita phalloides* or other toxic mushrooms, aflatoxin, arsenic, Bordeaux mixture (copper salts and lime), vinyl chloride monomer; carbon tetrachloride, beryllium, dimethylformamide, dimethylnitrosamine, methylenedianiline, phosphorus, chlordecone (Kepone), 2,3,7,8-tetrachloro-dibenzo p-dioxin (TCDD), tetrachloroethane, tetrachloroethylene, 2,4,5-trinitrotoluene, 1,1,1-trichloroethane, toluene, and xylene, and known "herbal remedies," e.g., ephedrine and eugenol.

Symptoms of hepatitis can include fatigue, loss of appetite, stomach discomfort, and/or jaundice (yellowing of the skin and/or eyes). More detailed descriptions of hepatitis are provided, for example, in the *The Merck Manual of Diagnosis and Therapy*, 17$^{th}$ Edition, Section 4, Chapter 42, Section 4, Chapter 44, and Section 4, Chapter 40, the contents of which are expressly incorporated herein by reference in their entirety.

Skilled practitioners will appreciate that a patient can be diagnosed by a physician as suffering from hepatitis by any method known in the art, e.g., by assessing liver function, e.g., using blood tests for serum alanine aminotransferase (ALT) levels, alkaline phosphatase (AP), or bilirubin levels.

Individuals considered at risk for developing hepatitis may benefit particularly from the invention, primarily because prophylactic treatment can begin before there is any evidence of hepatitis. Individuals "at risk" include, e.g., patients infected with hepatitis viruses, or individuals suffering from any of the conditions or having the risk factors described herein (e.g., patients exposed to hepatotoxic agents). The skilled practitioner will appreciate that a patient can be determined to be at risk for hepatitis by a physician's diagnosis.

Amounts of CO effective to treat hepatitis can be administered to a patient on the day the patient is diagnosed as suffering from hepatitis or any condition associated with hepatitis, or as having any risk factor associated with an increased likelihood that the patient will develop hepatitis (e.g., that the patient has recently been, is being, or will be exposed to a hepatotoxic agent, e.g., a hepatotoxic drug such as acetaminophen). Patients can inhale CO at concentrations ranging from 10 ppm to 1000 ppm, e.g., about 100 ppm to about 800 ppm, about 150 ppm to about 600 ppm, or about 200 ppm to about 500 ppm. Preferred concentrations include, e.g., about 30 ppm, 50 ppm, 75 ppm, 100 ppm, 125 ppm, 200 ppm, 250 ppm, 500 ppm, 750 ppm, or about 1000 ppm. CO can be administered to the patient intermittently or continuously. CO can be administered for about 1, 2, 4, 6, 8, 10, 12, 14, 18, or 20 days, or greater than 20 days, e.g., 1 2, 3, 5, or 6 months, or until the patient no longer exhibits symptoms of hepatitis, or until the patient is diagnosed as no longer being at risk for hepatitis. In a given day, CO can be administered continuously for the entire day, or intermittently, e.g., a single whiff of CO per day (where a high concentration is used), or for up to 23 hours per day, e.g., up to 20, 15, 12, 10, 6, 3, or 2 hours per day, or up to 1 hour per day.

If the patient needs to be treated with a hepatotoxic drug (e.g., because prescribed by a physician), the patient can be treated with CO (e.g., a gaseous CO composition) before, during, and/or after administration of the drug. For example, CO can be administered to the patient, intermittently or continuously, starting 0 to 20 days before the drug is administered (and where multiple doses are given, before each individual dose), e.g., starting at least about 30 minutes, e.g., about 1, 2, 3, 5, 7, or 10 hours, or about 1, 2, 4, 6, 8, 10, 12, 14, 18, or 20 days, or greater than 20 days, before the administration. Alternatively or in addition, CO can be administered to the patient concurrent with administration of the drug. Alternatively or in addition, CO can be administered to the patient after administration of the drug, e.g., starting immediately after administration, and continuing intermittently or continuously for about 1, 2, 3, 5, 7, or 10 hours, or about 1, 2, 5, 8, 10, 20, 30, 50, or 60 days, indefinitely, or until a physician determines that administration of CO is no longer necessary (e.g., after the hepatotoxic drug is eliminated from the body or can no longer cause damage to the liver).

Preparation of Gaseous Compositions

A carbon monoxide composition may be a gaseous carbon monoxide composition. Compressed or pressurized gas useful in the methods of the invention can be obtained from any commercial source and in any type of vessel appropriate for storing compressed gas. For example, compressed or pressurized gases can be obtained from any source that supplies compressed gases, such as oxygen, for medical use. The term "medical grade" gas, as used herein, refers to gas suitable for administration to patients as defined herein. The pressurized gas including CO used in the methods of the present invention can be provided such that all gases of the desired final composition (e.g., CO, He, NO, $CO_2$, $O_2$, $N_2$) are in the same vessel, except that NO and $O_2$ cannot be stored together. Optionally, the methods of the present invention can be performed using multiple vessels containing individual gases. For example, a single vessel can be provided that contains carbon monoxide, with or without other gases, the contents of which can be optionally mixed with room air or with the contents of other vessels, e.g., vessels containing oxygen, nitrogen, carbon dioxide, compressed air, or any other suitable gas or mixtures thereof.

Gaseous compositions administered to a patient according to the present invention typically contain 0% to about 79% by weight nitrogen, about 21% to about 100% by weight oxygen and about 0.0000001% to about 0.3% by weight (corresponding to about 1 ppb or 0.001 ppm to about 3,000 ppm) carbon monoxide. Preferably, the amount of nitrogen in the gaseous composition is about 79% by weight, the amount of oxygen is about 21% by weight and the amount of carbon monoxide is about 0.0001% to about 0.25% by weight, preferably at least about 0.001%, e.g., at least about 0.005%, 0.010%, 0.02%, 0.025%, 0.03%, 0.04%, 0.05%, 0.06%, 0.08%, 0.10%, 0.15%, 0.20%, 0.22%, or 0.24% by weight. Preferred ranges of carbon monoxide include about 0.005% to about 0.24%, about 0.01% to about 0.22%, about 0.015% to about 0.20%, about 0.08% to about 0.20%, and about 0.025% to about 0.1% by weight. It is noted that gaseous carbon monoxide compositions having concentrations of carbon monoxide greater than 0.3% (such as 1% or greater) may be used for short periods (e.g., one or a few breaths), depending upon the application.

A gaseous carbon monoxide composition may be used to create an atmosphere that comprises carbon monoxide gas. An atmosphere that includes appropriate levels of carbon monoxide gas can be created, for example, by providing a vessel containing a pressurized gas comprising carbon monoxide gas, and releasing the pressurized gas from the vessel into a chamber or space to form an atmosphere that includes the carbon monoxide gas inside the chamber or space. Alternatively, the gases can be released into an apparatus that culminates in a breathing mask or breathing tube, thereby creating an atmosphere comprising carbon monoxide gas in the breathing mask or breathing tube, ensuring the patient is the only person in the room exposed to significant levels of carbon monoxide.

Carbon monoxide levels in an atmosphere can be measured or monitored using any method known in the art. Such methods include electrochemical detection, gas chromatography, radioisotope counting, infrared absorption, colorimetry, and electrochemical methods based on selective membranes (see, e.g., Sunderman et al., Clin. Chem. 28:2026-2032, 1982; Ingi et al., Neuron 16:835-842, 1996). Sub-parts per million carbon monoxide levels can be detected by, e.g., gas chromatography and radioisotope counting. Further, it is known in the art that carbon monoxide levels in the sub-ppm range can be measured in biological tissue by a midinfrared gas sensor (see, e.g., Morimoto et al., Am. J. Physiol. Heart. Circ. Physiol 280:H482-H488, 2001). Carbon monoxide sensors and gas detection devices are widely available from many commercial sources.

Preparation of Liquid Compositions

A carbon monoxide composition may also be a liquid carbon monoxide composition. A liquid can be made into a carbon monoxide composition by any method known in the art for causing gases to become dissolved in liquids. For example, the liquid can be placed in a so-called "$CO_2$ incubator" and exposed to a continuous flow of carbon monoxide, preferably balanced with carbon dioxide, until a desired concentration of carbon monoxide is reached in the liquid. As another example, carbon monoxide gas can be "bubbled" directly into the liquid until the desired concentration of carbon monoxide in the liquid is reached. The amount of carbon monoxide that can be dissolved in a given aqueous solution increases with decreasing temperature. As still another example, an appropriate liquid may be passed through tubing that allows gas diffusion, where the tubing runs through an atmosphere comprising carbon monoxide (e.g., utilizing a device such as an extracorporeal membrane oxygenator). The carbon monoxide diffuses into the liquid to create a liquid carbon monoxide composition.

It is likely that such a liquid composition intended to be introduced into a living animal will be at or about 37° C. at the time it is introduced into the animal.

The liquid can be any liquid known to those of skill in the art to be suitable for administration to patients (see, for example, Oxford Textbook of Surgery, Morris and Malt, Eds., Oxford University Press (1994)). In general, the liquid will be an aqueous solution. Examples of solutions include Phosphate Buffered Saline (PBS), Celsior™, Perfadex™, Collins solution, citrate solution, and University of Wisconsin (UW) solution (Oxford Textbook of Surgery, Morris and Malt, Eds., Oxford University Press (1994)). In one embodiment of the present invention, the liquid is Ringer's Solution, e.g., lactated Ringer's Solution, or any other liquid that can be used infused into a patient. In another embodiment, the liquid includes blood, e.g., whole blood.

Any suitable liquid can be saturated to a set concentration of carbon monoxide via gas diffusers. Alternatively, pre-made solutions that have been quality controlled to contain set levels of carbon monoxide can be used. Accurate control of dose can be achieved via measurements with a gas permeable, liquid impermeable membrane connected to a carbon monoxide analyzer. Solutions can be saturated to desired effective concentrations and maintained at these levels.

Treatment of Patients with Carbon Monoxide Compositions

A patient can be treated with a carbon monoxide composition by any method known in the art of administering gases and/or liquids to patients. Carbon monoxide compositions can be administered to a patient diagnosed with, or determined to be at risk for, hepatitis. The present invention contemplates the systemic administration of liquid or gaseous carbon monoxide compositions to patients (e.g., by inhalation and/or ingestion), and the topical administration of the compositions to the patient's liver (e.g., by introduction into the abdominal cavity).

Systemic Delivery of Carbon Monoxide

Gaseous carbon monoxide compositions can be delivered systemically to a patient, e.g., a patient diagnosed with, or determined to be at risk for hepatitis. Gaseous carbon monoxide compositions are typically administered by inhalation through the mouth or nasal passages to the lungs, where the carbon monoxide is readily absorbed into the patient's bloodstream. The concentration of active compound (CO) utilized in the therapeutic gaseous composition will depend on absorption, distribution, inactivation, and excretion (generally, through respiration) rates of the carbon monoxide as well as other factors known to those of skill in the art. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. Treatments can be monitored and CO dosages can be adjusted to ensure optimal treatment of the patient. Acute, sub-acute and chronic administration of carbon monoxide are contemplated by the present invention, depending upon, e.g., the severity or persistence of hepatitis in the patient. Carbon monoxide can be delivered to the patient for a time (including indefinitely) sufficient to treat the condition and exert the intended pharmacological or biological effect.

The following are examples of some methods and devices that can be utilized to administer gaseous carbon monoxide compositions to patients.

Ventilators

Medical grade carbon monoxide (concentrations can vary) can be purchased mixed with air or another oxygen-containing gas in a standard tank of compressed gas (e.g., 21% $O_2$, 79% $N_2$). It is non-reactive, and the concentrations that are required for the methods of the present invention are well below the combustible range (10% in air). In a hospital setting, the gas presumably will be delivered to the bedside where it will be mixed with oxygen or house air in a blender to a desired concentration in ppm (parts per million). The patient will inhale the gas mixture through a ventilator, which will be set to a flow rate based on patient comfort and needs. This is determined by pulmonary graphics (i.e., respiratory rate, tidal volumes etc.). Fail-safe mechanism(s) to prevent the patient from unnecessarily receiving greater than desired amounts of carbon monoxide can be designed into the delivery system. The patient's carbon monoxide level can be monitored by studying (1) carboxyhemoglobin (COHb), which can be measured in venous blood, and (2) exhaled carbon monoxide collected from a side port of the ventilator. Carbon monoxide exposure can be adjusted based upon the patient's health status and on the basis of the markers. If necessary, carbon monoxide can be washed out of the patient by switching to 100% $O_2$ inhalation. Carbon monoxide is not metabolized; thus, whatever is inhaled will ultimately be exhaled except for a very small percentage that is converted to $CO_2$. Carbon monoxide can also be mixed with any level of $O_2$ to provide therapeutic delivery of carbon monoxide without consequential hypoxic conditions.

Face Mask and Tent

A carbon monoxide-containing gas mixture is prepared as above to allow passive inhalation by the patient using a facemask or tent. The concentration inhaled can be changed and can be washed out by simply switching over to 100% $O_2$. Monitoring of carbon monoxide levels would occur at or near the mask or tent with a fail-safe mechanism that would prevent too high of a concentration of carbon monoxide from being inhaled.

Portable Inhaler

Compressed carbon monoxide can be packaged into a portable inhaler device and inhaled in a metered dose, for example, to permit intermittent treatment of a recipient who is not in a hospital setting. Different concentrations of carbon monoxide could be packaged in the containers. The device could be as simple as a small tank (e.g., under 5 kg) of appropriately diluted CO with an on-off valve and a tube from which the patient takes a whiff of CO according to a standard regimen or as needed.

Intravenous Artificial Lung

An artificial lung (a catheter device for gas exchange in the blood) designed for $O_2$ delivery and $CO_2$ removal can be used for carbon monoxide delivery. The catheter, when implanted, resides in one of the large veins and would be able to deliver carbon monoxide at given concentrations either for systemic delivery or at a local site. The delivery can be a local delivery of a high concentration of carbon monoxide for a short period of time at the site of the procedure, e.g., in proximity to the liver (this high concentration would rapidly be diluted out in the bloodstream), or a relatively longer exposure to a lower concentration of carbon monoxide (see, e.g., Hattler et al., Artif. Organs 18(11):806-812 (1994); and Golob et al., ASAIO J., 47(5): 432-437 (2001)).

Normobaric Chamber

In certain instances, it would be desirable to expose the whole patient to carbon monoxide. The patient would be inside an airtight chamber that would be flooded with carbon monoxide (at a level that does not endanger the patient, or at a level that poses an acceptable risk without the risk of bystanders being exposed. Upon completion of the exposure, the chamber could be flushed with air (e.g., 21% $O_2$, 79% $N_2$) and samples could be analyzed by carbon monoxide analyzers to ensure no carbon monoxide remains before allowing the patient to exit the exposure system.

Systemic Delivery of Liquid CO Compositions

The present invention further contemplates that aqueous solutions comprising carbon monoxide can be created for systemic delivery to a patient, e.g., for oral delivery and/or by infusion into the patient, e.g., intravenously, intra-arterially, intraperitoneally, and/or subcutaneously. For example, liquid CO compositions, such as CO-saturated Ringer's Solution, can be infused into a patient suffering from or at risk for hepatitis. Alternatively or in addition, CO-partially or completely saturated whole (or partial) blood can be infused into the patient.

The present invention also contemplates that agents capable of delivering doses of gaseous CO compositions or liquid CO compositions can be utilized (e.g., CO-releasing gums, creams, ointments, lozenges, or patches).

Topical Treatment of Organs with Carbon Monoxide

Alternatively or in addition, carbon monoxide compositions can be applied directly to the liver, e.g., to the entire liver, or to any portion thereof. A gaseous composition can be directly applied to the liver of a patient by any method known in the art for insufflating gases into a patient. For example, gases, e.g., carbon dioxide, are often insufflated into the abdominal cavity of patients to facilitate examination during laparoscopic procedures (see, e.g., Oxford Textbook of Surgery, Morris and Malt, Eds., Oxford University Press (1994)). The skilled practitioner will appreciate that similar procedures could be used to administer carbon monoxide compositions directly to the liver of a patient.

Aqueous carbon monoxide compositions can also be administered topically to the liver of a patient. Aqueous forms of the compositions can be administered by any method known in the art for administering liquids to patients. As with gaseous compositions, aqueous compositions can be applied directly to the liver. For example, liquids, e.g., saline solutions containing dissolved CO, can be injected into the abdominal cavity of patients during laparoscopic procedures. The skilled practitioner will appreciate that similar procedures could be used to administer liquid carbon monoxide compositions directly to the liver of a patient. Further, an in situ exposure can be carried out by flushing the liver or a portion thereof with a liquid carbon monoxide composition (see Oxford Textbook of Surgery, Morris and Malt, Eds., Oxford University Press (1994)).

Use of Hemoxygenase-1, Other Compounds, and Other Treatments for Hepatitis

Also contemplated by the present invention is the induction or expression of hemeoxygenase-1 (HO-1) in conjunction with administration of CO. For example, HO-1 can be induced in a patient suffering from or at risk for hepatitis. As used herein, the term "induce(d)" means to cause increased production of a protein, e.g., HO-1, in isolated cells or the cells of a tissue, organ or animal using the cells' own endogenous (e.g., non-recombinant) gene that encodes the protein.

HO-1 can be induced in a patient by any method known in the art. For example, production of HO-1 can be induced by hemin, by iron protoporphyrin, or by cobalt protoporphyrin. A variety of non-heme agents including heavy metals, cytokines, hormones, NO, $CoCl_2$, endotoxin and heat shock are also strong inducers of HO-1 expression (Choi et al., Am. J. Respir. Cell Mol. Biol. 15:9-19, 1996; Maines, Annu Rev. Pharmacol. Toxicol. 37:517-554, 1997; and Tenhunen et al., J. Lab. Clin. Med. 75:410-421, 1970). HO-1 is also highly induced by a variety of agents causing oxidative stress, including hydrogen peroxide, glutathione depletors, UV irradiation, endotoxin and hyperoxia (Choi et al., Am. J. Respir. Cell Mol. Biol. 15:9-19, 1996; Maines, Annu Rev. Pharmacol. Toxicol. 37:517-554, 1997; and Keyse et al., Proc. Natl. Acad. Sci. USA 86:99-103, 1989). A "pharmaceutical composition comprising an inducer of HO-1" means a pharmaceutical composition containing any agent capable of inducing HO-1 in a patient, e.g., any of the agents described above, e.g., NO, hemin, iron protoporphyrin, and/or cobalt protoporphyrin.

HO-1 expression in a cell can be increased via gene transfer. As used herein, the term "express(ed)" means to cause increased production of a protein, e.g., HO-1 or ferritin, in isolated cells or the cells of a tissue, organ or animal using an exogenously administered gene (e.g., a recombinant gene). The HO-1 or ferritin is preferably of the same species (e.g., human, mouse, rat, etc.) as the recipient, in order to minimize any immune reaction. Expression could be driven by a constitutive promoter (e.g., cytomegalovirus promoters) or a tissue-specific promoter (e.g., milk whey promoter for mammary cells or albumin promoter for liver cells). An appropriate gene therapy vector (e.g., retrovirus, adenovirus, adeno associated virus (AAV), pox (e.g., vaccinia) virus, human immunodeficiency virus (HIV), the minute virus of mice, hepatitis B virus, influenza virus, Herpes Simplex Virus-1, and lentivirus) encoding HO-1 or ferritin would be administered to a patient suffering from or at risk for hepatitis, by mouth, by inhalation, or by injection into the liver. Similarly, plasmid vectors encoding HO-1 or apoferritin can be administered, e.g., as naked DNA, in liposomes, or in microparticles.

Further, exogenous HO-1 protein can be directly administered to a patient by any method known in the art. Exogenous HO-1 can be directly administered in addition, or as an alternative, to the induction or expression of HO-1 in the patient as described above. The HO-1 protein can be delivered to a patient, for example, in liposomes, and/or as a fusion protein, e.g., as a TAT-fusion protein (see, e.g., Becker-Hapak et al., Methods 24:247-256, 2001).

Alternatively or in addition, any of the products of metabolism by HO-1, e.g., bilirubin, biliverdin, iron, and/or ferritin, can be administered to a patient in conjunction with CO in order to prevent or treat hepatitis. Further, the present invention contemplates that iron-binding molecules other than ferritin, e.g., desferoxamine (DFO), iron dextran, and/or apoferritin, can be administered to the patient. Further still, the present invention contemplates that enzymes (e.g., biliverdin reductase) that catalyze the breakdown any of these products can be inhibited to create/enhance the desired effect. Any of the above can be administered, e.g., orally, intravenously, intraperitoneally, or by direct administration to the liver.

The present invention contemplates that compounds that release CO into the body after administration of the compound (e.g., CO-releasing compounds, e.g., photoactivatable CO-releasing compounds), e.g., dimanganese decacarbonyl, tricarbonyldichlororuthenium (II) dimer, and methylene chloride (e.g., at a dose of between 400 to 600 mg/kg, e.g., about 500 mg/kg), can also be used in the methods of the present invention, as can carboxyhemoglobin and CO-donating hemoglobin substitutes.

The above can be administered to a patient in any way, e.g., by oral, intraperitoneal, intravenous, or intraarterial administration. Any of the above compounds can be administered to the patient locally and/or systemically, and in any combination.

The present invention further contemplates treating/preventing hepatitis by administering CO to the patient in combination with any other known methods or compounds for treating hepatitis, e.g., cessation or reducing administration of causative drugs; administering corticosteroids and/or α-interferon or other antiviral agents to the patient; and/or performing surgery on the patient, e.g., liver transplantation.

The invention is illustrated in part by the following examples, which are not to be taken as limiting the invention in any way.

EXAMPLE 1

Carbon Monoxide Attenuates Liver Injury

Animals

Male C57BL/6J (Charles Rivers Laboratories, Bar Harbor, Me.), 8-12-wk-old inos$^{-/-}$ mice and wild type littermates (bred/maintained at the University of Pittsburgh) were used for in vivo experiments.

Acute Hepatic Injury Models

Groups of mice were administered TNF-α/D-gal (0.3 µg/8 mg/mouse, i.p., respectively). Depending on the experimental condition, some mice received CO (250 ppm), the selective NO donor $O_2$-vinyl 1-(pyrrolidin-1-yl)diazen-1-ium-1,2-diolate (V-PYRRO; 10 mg/kg subcutaneously (s.c.), Alexis Biochem., San Diego, Calif.) or cobalt protoporphyrin (CoPP, 5 mg/kg, intraperitoneally (i.p.), Frontier Scientific, Logan, Utah). Additionally, the selective inhibitor of iNOS L-N6-(1-iminoethyl)-lysine-dihydrochloride (L-NIL; 5 mg/kg, i.p., Alexis Biochemicals) or the HO-1 inhibitor tin protoporphyrin (SnPP; 50 µmol/kg, i.p., Frontier Scientific) was administered when specified. Where indicated, acetaminophen (Sigma Chem. Co.; St Louis, Mo.) was administered (500 mg/kg, i.p.).

Hepatocyte Cell Culture

Mouse primary hepatocytes were harvested from C57BL/6J, mkk3$^{-/-}$, inos$^{-/-}$ (in-house breeding colony), or hmox-1$^{-/-}$ mice as described in Kim et al. (J. Biol. Chem. 272: 1402-1411 (1997)). Hepatocytes were used on days 1-3 following harvest.

Induction of Hepatocyte Death/Apoptosis

Cells were treated with TNF-α (10 ng/ml) and actinomycin-D (Act-D; 200 ng/ml, Sigma Chemical Co. St. Louis, Mo.) to induce cell death. TNF-α/ActD treatment has been demonstrated to induce cell death, specifically apoptosis, in primary hepatocytes (see, e.g., Kim et al. (J. Biol. Chem.

272: 1402-1411 (1997)). Hepatocytes were treated with CO, the NO donor s-nitroso-N-acetyl-penicillamine (SNAP; 250-750 μM), and/or additional pharmacologic agents where indicated. Twelve hours after TNF-α/ActD treatment, cells were washed and stained with crystal violet to determine viability as previously described (Id.). Where indicated, the selective in vitro inhibitor of iNOS, L-N5-(1-iminoethyl)-ornithine-2HCl (LNIO; 1-2 mM; Calbiochem, San Diego, Calif.) was administered.

Gene Transfer/Plasmids.

In some experiments, gene transfer of an IκBα superrepressor (Hellerbrand et al., Hepatology 27:1285-1295 (1998)) or β-galactosidase using adenoviral vectors (10 pfu/cell) was performed 12 hours prior to TNF-α/ActD treatment. NF-κB activation was evaluated using a luciferase reporter assay as described in Chow et al. (J. Biol. Chem. 274: 10689-10692 (1999)). Briefly, hepatocytes were co-transfected with NF-κB reporter constructs (pGL3-kappaβ luciferase, 100 ng/well; and pIEP-Lac-z 0.5 μg/well) using Lipofectin™ (Invitrogen, Carlsbad, Calif.) as instructed by the manufacturer. Evaluation of iNOS expression was performed using a luciferase reporter assay as described in Lowenstein et al. (Proc. Natl. Acad. Sci. U.S.A 90: 9730-9734 (1993)). Briefly, hepatocytes were co-transfected with iNOS promoter reporter constructs (pXP2; 1 μg/well) and pIEP-LacZ (0.5 μg/well) as described above.

Luciferase Reporter Assays

Hepatocytes were transfected with plasmids as described above and treated with various stimuli 24 hours after transfection. Luciferase activity (reported as arbitrary units; A.U.) was assayed 6 hours after initiation of treatment, using a luciferase assay kit (Promega, Madison, Wis.) and a Berthold Luminometer. Results were corrected for transfection efficiency and protein concentration.

Electrophoretic Mobility Shift Assay

Nuclei were extracted from hepatocytes following treatment. A double-stranded DNA NF-κB consensus sequence (GGGGACTTTCCC (SEQ ID NO:1)); Santa Cruz Biotechnology, Santa Cruz, Calif.) was labelled with [δ-$^{32}$P]-ATP and incubated with 5 mg of total nuclear protein. Some incubations were performed in the presence of antibodies against p65/Rel A or p50 (Santa Cruz Biotech) to evaluate for supershift. Electrophoretic mobility shift assay (EMSAs) were performed as described in Taylor et al. (J. Biol. Chem. 273:15148-15156 (1998)).

Immunoblot Analysis

Western blot analysis was performed on primary hepatocytes in culture or from liver homogenates with antibodies to iNOS (Transduction Laboratories, Lexington, Ky.; 1:1000), HO-1 (Calbiochem; 1:2000), or β-actin (Sigma Chemical; 1:5000). Thirty μg protein in cell culture experiments or 100 μg protein from liver homogenates was loaded per well for SDS-PAGE.

Histology/Immunohistochemistry

For histology and immunohistochemistry, livers were fixed in 2% paraformaldehyde and then snap frozen in liquid nitrogen. Livers were then sectioned (7 microns thick) and stained with hematoxylin and eosin (H&E). Liver sections were also stained for TUNEL and activated caspase-3 using kits according to the manufacturer's instructions (Promega). Sections for iNOS immunocytochemistry were blocked with 5% goat serum containing 0.2% bovine serum albumin. Thereafter, sections were incubated for 1 hour at room temperature with anti-iNOS antibody (Transduction Laboratories; 1:300), then washed and probed with a secondary antibody conjugated to Alexa-488 (Molecular Probes, Eugene, Oreg.). Nuclei were stained with Hoechst dye.

Images were acquired using an Olympus Provus microscope. Hepatocytes in culture were plated on gelatinized coverslips, stimulated as indicated, and then fixed in 2% paraformaldehyde containing 0.1% Triton X-100. Blocking and staining was similar to liver sections except anti-p65/Rel A antibody (Santa Cruz Biotechnology; 1:350) was utilized.

CO Exposure

The animals were exposed to CO at a concentration of 250 ppm. Briefly, 1% CO in air was mixed with air (21% oxygen) in a stainless steel mixing cylinder and then directed into a 3.70 ft$^3$ glass exposure chamber at a flow rate of 12 L/min. A CO analyzer (Interscan, Chatsworth, Calif.) was used to measure CO levels continuously in the chamber. CO concentrations were maintained at 250 ppm at all times. Mice were placed in the exposure chamber as required.

HO-1 Protects Against Liver Injury

Whether HO-1 is protective against acute hepatic failure was investigated. The results are presented in FIG. 1. Cobalt protoporphyrin (5 mg/kg, i.p.) was administered to male C57BL/6J mice. Twenty-four hours later, TNF-α/D-gal (0.3 μg/8 mg/mouse, i.p., respectively) was administered to the mice. Serum alanine aminotransferase (ALT) levels in the mice were measured 8 hours after administration of TNF-α/D-gal. Induction of HO-1 prevented liver injury as measured by serum ALT levels.

Exogenous CO Protects Hepatocytes

Whether exogenous CO is protective against hepatocyte cell death in vitro was investigated. The results are presented in FIGS. 2 and 3. To generate the data presented in FIG. 2, mouse hepatocytes were pre-incubated with CO (250 ppm) for 1 hr (standard pre-treatment time for all experiments) prior to addition of TNF-α/Act-D (10 ng/200 ng/ml respectively). Cells were maintained in CO for the duration of the experiment. Twelve hours afterward, cell viability was measured as described in Kim et al. (J. Biol. Chem. 272: 1402-1411 (1997)). Adenoviral experiments involved incubating hepatocytes overnight with 10 pfu/cell of the adenovirus prior to addition of TNF-α/ActD, and then assaying for viability using crystal violet. The roles of signaling molecules guanylyl cyclase and p38 MAPK were also investigated in this model. To evaluate the role of cGMP and confirm the role of NF-κB, hepatocytes were treated separately with the soluble guanylate cyclase (sGC) inhibitor 1H-[1,2,4]Oxadiazolo[4,3-a]quinoxalin-1-one (ODQ; Calbiochem; 2-10 μM) or the NF-κB inhibitor BAY 11-7082, (10 μM). Cells were treated with the inhibitors for 1 hour prior to the 1 hour pretreatment with CO. TNF-α/ActD was then added and the cells tested for viability 12 hours later. NF-κB activation was critical to the protection elicited by CO while cGMP was not involved. Exposure to CO led to significantly less cell death (*p<0.01) than without CO.

Figure 3:
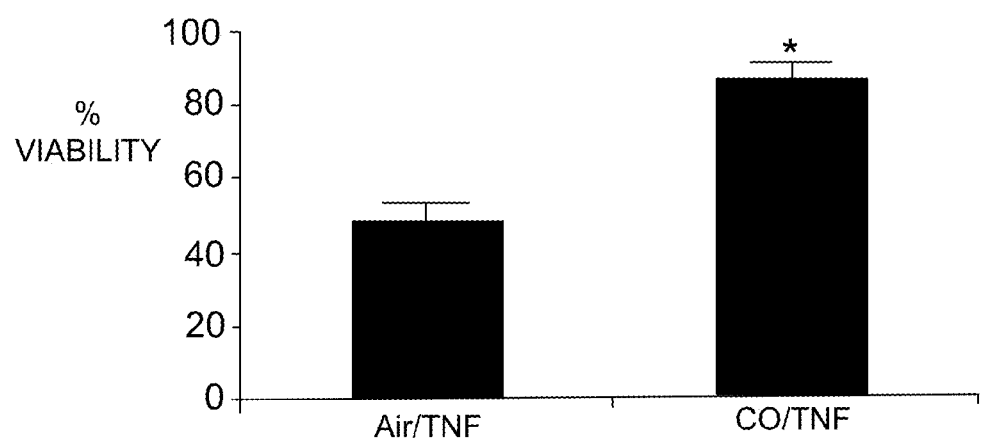
FIG. 3 is a bar graph illustrating that exogenous CO protects human hepatocytes against TNF-α/Actinomycin-D (ActD)-induced cell death. CO=carbon monoxide; Air=room air; TNF=TNF-α/ActD. Results are mean±SD of triplicate wells from 3 independent experiments. p<0.05.

To generate the data presented in FIG. 3, human primary hepatocytes obtained from a donor liver resection were treated with CO and TNF-α/ActD as described above.

Figure 2:
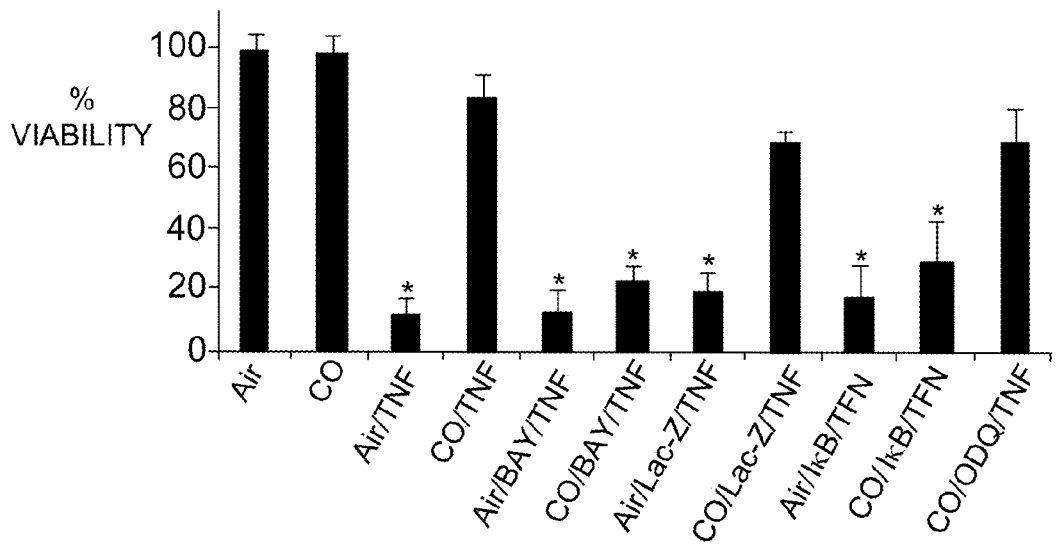
FIG. 2 is a bar graph illustrating that exogenous CO protects hepatocytes against TNF-α-induced cell death in a cGMP/p38 pathway-independent and an NF-κB activation-dependent manner. CO=carbon monoxide; Air=room air; TNF=tumor necrosis factor alpha; BAY=BAY 11-7082 (inhibits NF-kB activation); IκB=IκBα (prevents NF-κB activation); ODQ=1H-[1,2,4]Oxadiazolo[4,3-a]quinoxalin-1-one (a selective guanylyl cyclase inhibitor); Lac-Z=pIEP-Lac-Z (adenoviral control). Results shown are the mean±SD of triplicate wells from four independent experiments (*p<0.01).

Exposure of primary mouse, rat, and human hepatocytes to CO inhibited TNF-α induced apoptosis Inhibition of hepatocyte apoptosis was independent of cGMP generation, as the selective guanylyl cyclase inhibitor ODQ did not reverse the protection provided by CO (FIG. 2). Additionally, CO treatment inhibited cell death both in the presence of SB203580 (3-30 μM, Calbiochem), a selective inhibitor of p38 MAPK activation, and in hepatocytes from mkk3$^{-/-}$ mice, the dominant upstream kinase for p38 (data not shown). Thus, the effects of CO were independent of the cGMP/p38 MAPK pathway. In these experiments, hepatocytes were pre-treated with CO for one hour prior to addition of TNF-α/ActD to the medium. If CO treatment was initiated after addition of TNF-α, less protection was observed (data not shown).

The Role of NF-κB in CO Protection

Whether CO-induced protection of hepatocytes depends upon NF-κB was investigated. FIGS. 4, 5, and 6A-6C present data illustrating that that CO induced an increase in NF-κB nuclear translocation and DNA binding in mouse hepatocytes as measured by NF-κB luciferase reporter assay activity, EMSA, and immunostaining for Rel A/p65 nuclear translocation, respectively.

Figure 4:
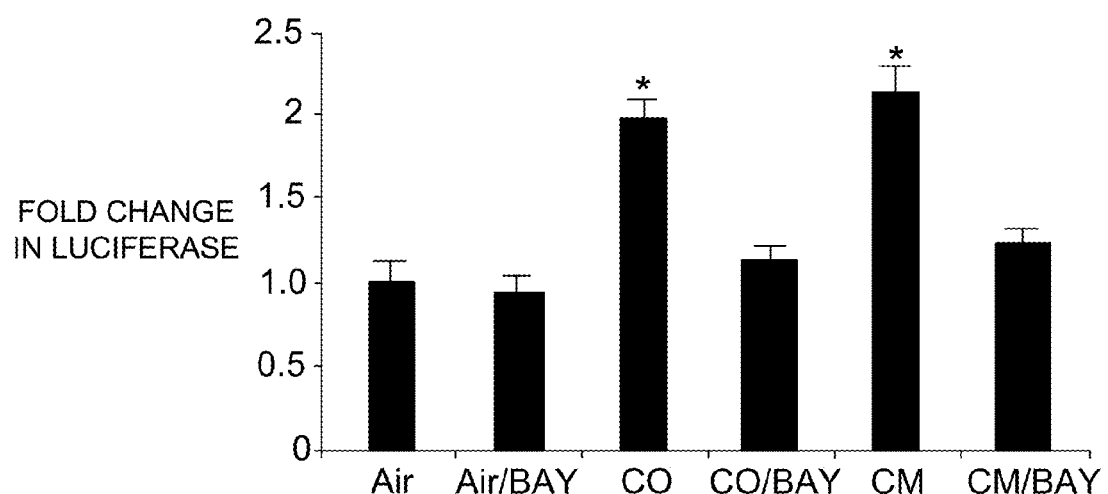
FIG. 4 is a bar graph illustrating that exogenous CO causes an increase in NF-κB activation in hepatocytes. CO=carbon monoxide; Air=room air; BAY=BAY 11-7082; CM=cytokine mixture (TNF-α (500 U/ml), IL-1β (100 U/ml), and IFN-δ (100 U/ml)). Results shown are the mean±SE of triplicate wells from three independent experiments. *p<0.001 versus Air.

To generate the data presented in FIG. 4, evaluation of NF-κB activation was performed using a luciferase reporter assay as described in Chow et al. (J. Biol. Chem. 274: 10689-10692 (1999)). Briefly, hepatocytes were co-transfected with NF-κB reporter constructs and pIEP-Lac-z 24 hr prior to addition of BAY 11-7082 (10 μM) or vehicle. Cells were incubated for 1 hr prior to CO (250 ppm). Luciferase activity (reported as arbitrary units; A.U.) was assayed 6 hr after exposure to CO or a cytokine mixture (CM) composed of TNF-α (500 U/ml), IL-1β (100 U/ml), and IFN-δ (100 U/ml), which was used as a positive control for NF-κB activation. Results were corrected for transfection efficiency and protein concentration.

Figure 5:
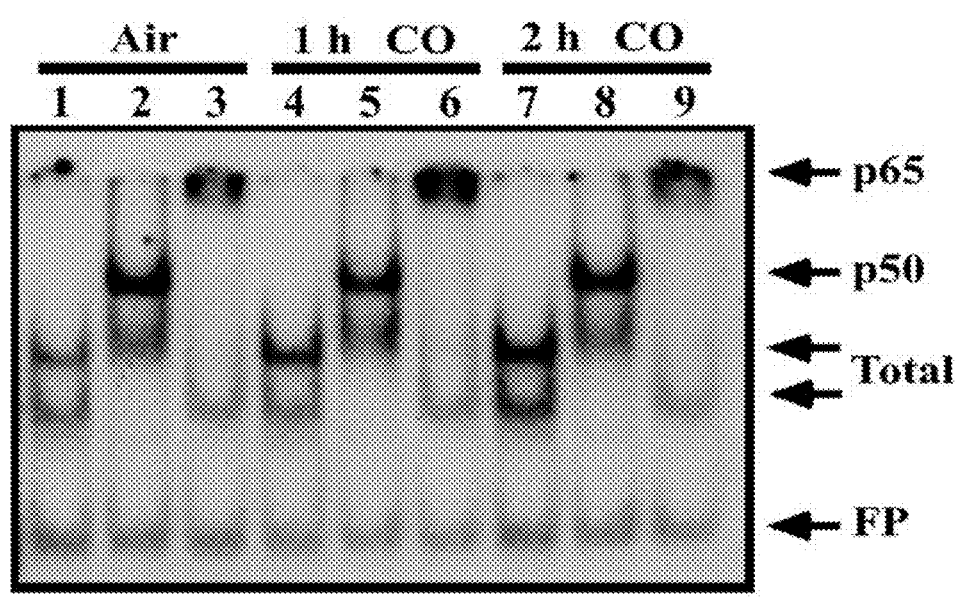
FIG. 5 is a picture of a polyacrylamide gel illustrating that exogenous CO induces an increase in NF-κB nuclear translocation and DNA binding as measured by electrophoretic mobility shift assay (EMSA). FP=free probe (no nuclear protein, thus no DNA binding); TOTAL=NFkB bands without antibody supershifting.

To generate the data in FIG. 5, NF-κB DNA binding was evaluated using EMSA in hepatocytes treated with CO (250 ppm). Note the time-dependent increase in NF-κB binding (total) with expression peaking at one hr (Lanes 1, 4, 7). Extracts were then supershifted to identify the different NF-κB dimers using antibodies against p50 (Lanes 2, 5, 8) and p65 (Lanes 3, 6, 9).

To generate the data in FIGS. 6A-6C, primary hepatocytes were immunostained for nuclear p65 localization following exposure to 1 hr CO (250 ppm). Images depict nuclear translocation of NF-κB (arrows pointing to green nuclei that depict the translocation of NF-κB) in both CM (used as a positive control) and CO-treated cells versus no localization in air treated cells (arrows pointing to blue nuclei).

NF-κB luciferase reporter assay activity peaked one hour after placing cells in the CO atmosphere. A cytokine mixture (CM) was included in the treatment groups as a positive signal as well as a standard for maximum reporter activity by which to evaluate the effects of CO. Transfection efficiency in primary hepatocytes is difficult, but the reporter activity was very significant (*p<0.001 versus control). These data combined with the positive immunostaining and EMSA results support the notion that CO induces a moderate increase in NF-κB that in itself may in part result in selective gene expression. To evaluate whether NF-κB activity is needed for protection mediated by CO, adenoviral gene transfer of IκBα was utilized to prevent NF-κB translocation and BAY 11-7082 (1-10 mM, Calbiochem) was used to inhibit NF-κB activation. The protective effects of CO were abrogated by inhibition of NF-κB activation.

The Role of NF-κB-Dependent iNOS Expression in CO Protection

Whether CO-mediated protection of hepatocytes requires expression of iNOS and generation of NO was investigated. The results are presented in FIGS. 7, 8, and 9.

Figure 7:
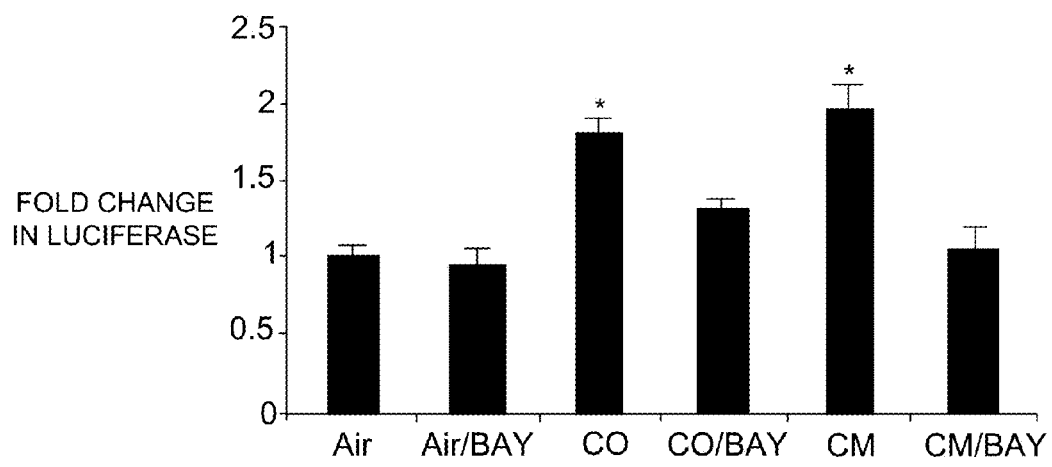
FIG. 7 is a bar graph illustrating that exogenous CO-induced protection of hepatocytes involves NF-κB-dependent iNOS expression. CO=carbon monoxide; Air=room air; BAY=BAY 11-7082; CM=cytokine mixture. Results shown are the mean±SE of triplicate wells from four independent experiments. *p<0.001 versus air and air/BAY-treated cells.

To generate the data in FIG. 7, evaluation of iNOS expression was performed using a luciferase reporter assay as described in Lowenstein et al. (Proc. Natl. Acad. Sci. U.S.A 90: 9730-9734 (1993)). Briefly, hepatocytes were co-transfected with an iNOS promoter reporter construct and pIEP-LacZ 24 hr prior to exposure to BAY 11-7082 (10 μM) or vehicle. Cells were incubated with BAY 1 hr prior to exposure to CO (250 ppm). Luciferase activity (reported as arbitrary units; A.U.) was assayed as above. Cytokine mixture (CM; see above) was used as a positive control to induce iNOS expression, and results were corrected for transfection efficiency and protein concentration.

Figure 8:
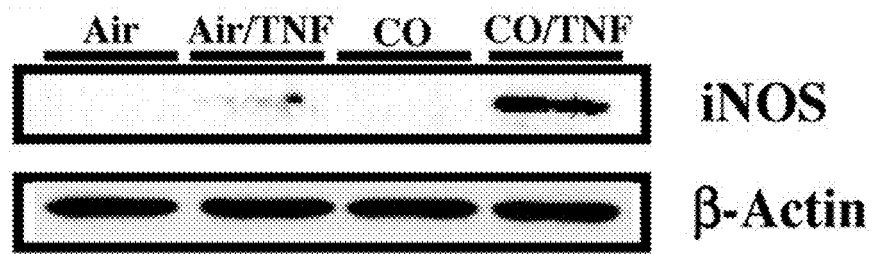
FIG. 8 is a picture of a Western blot illustrating that iNOS protein expression in hepatocytes is markedly increased by exposure to TNF-α in the presence of CO as compared to exposure to TNF-α alone. iNOS=inducible nitric oxide synthase; CO=carbon monoxide; Air=room air; TNF=TNF-α/ActD; β-Actin=control protein. The immunoblot is representative of 3 independent experiments.

To generate the data in FIG. 8, expression of iNOS protein was evaluated using immunoblotting techniques. Briefly, cell extracts from hepatocytes were treated with TNF-α/ActD for 6-8 hr in the presence and absence of CO (250 ppm). Control cells received air or CO alone. Note in FIG. 8 that TNF-α induces iNOS expression minimally, while those cells treated with TNF-α in the presence of CO show a significantly greater induction in iNOS protein.

Figure 9:
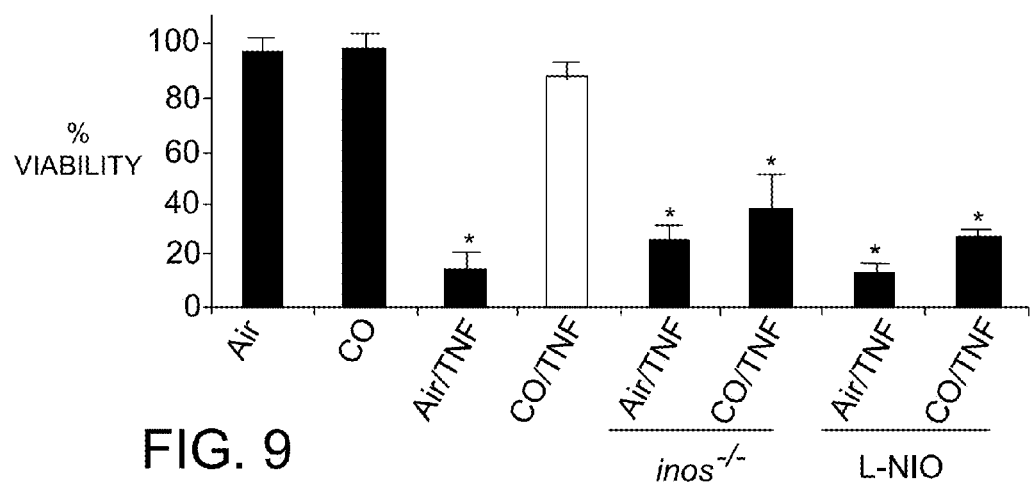
FIG. 9 is a bar graph illustrating that iNOS activity-deficient mouse (inos$^{-/-}$) hepatocytes are not protected by CO against TNF-α-induced cell death. CO=carbon monoxide; Air=room air; TNF=TNF-α/ActD; inos$^{-/-}$=iNOS knockout mice; L-NIO=L-N5-(1-iminoethyl)-ornithine-2HCl. Results shown are the mean±SE of triplicate wells from four independent experiments. *p<0.01 versus non-TNF/ActD and CO/TNF/ActD-treated cells.

To generate the data presented in FIG. 9, mouse hepatocytes were isolated from inos$^{-/-}$ or from wild type C57BL/6J mice, which were then pre-treated for 1 hr with L-NIO (1 mM) to inhibit iNOS prior to CO administration. Those groups exposed to CO received a one-hour pretreatment prior to addition of TNF-α/ActD and were then returned to CO exposure. CO did not provide protection against cell death, as evaluated via crystal violet exclusion 12 hr later, in cells where iNOS expression was absent or inhibited.

Exposure of hepatocytes to CO produced a highly significant increase in activity in an iNOS luciferase reporter assay (FIG. 7). Again, a cytokine mixture was used as both a positive control in these low efficiency transfections and as a standard by which to evaluate the effects of CO. Consistent with the NF-κB dependence of iNOS expression, decreased reporter activity was observed in hepatocytes treated with BAY 11-7082 (FIG. 7). Additionally, iNOS protein was markedly increased in response to TNF-α in the presence of CO compared to TNF-α alone (FIG. 8). Using hepatocytes from iNOS knockout mice (inos$^{-/-}$) and wild type hepatocytes treated with the selective iNOS inhibitor L-NIO (1 mM, Calbiochem), applicants investigated whether CO could protect against TNF-α-induced death in the absence of iNOS activity. Hepatocytes lacking iNOS activity were not protected by CO from TNF-α-induced cell death while wild type hepatocytes were protected (FIG. 9). Taken together, these data show that CO requires NF-κB activation and iNOS expression to protect hepatocytes from cell death in vitro.

Inhaled CO is Protective Against Liver Failure

Whether inhaled CO protects mice against liver injury in a TNF-α/D-gal model of fulminant hepatic failure was investigated. The results are presented in FIGS. 10 and 11A-11H.

Figure 10:
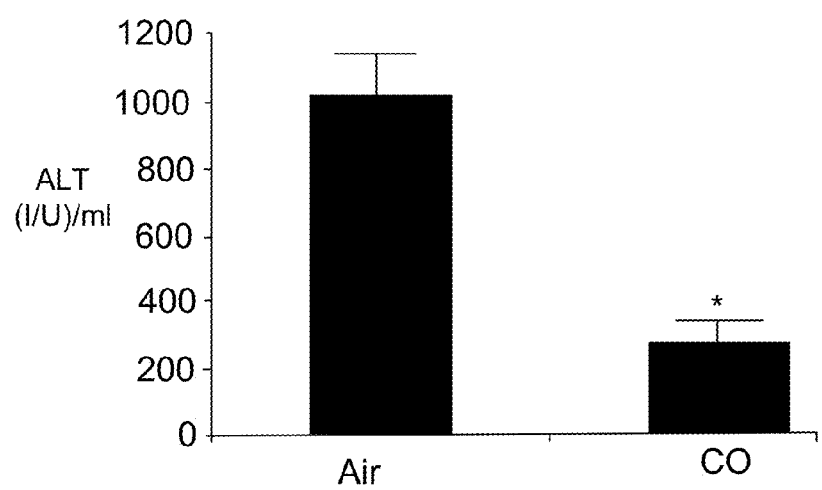
FIG. 10 is a bar graph illustrating that exogenously-administered CO prevents TNF-α/D-Gal-induced liver injury in mice. ALT=serum alanine aminotransferase; CO=carbon monoxide; Air=room air. Results presented as mean±SD of 18-20 mice. *p<0.001 versus air-treated.
Figure 11:
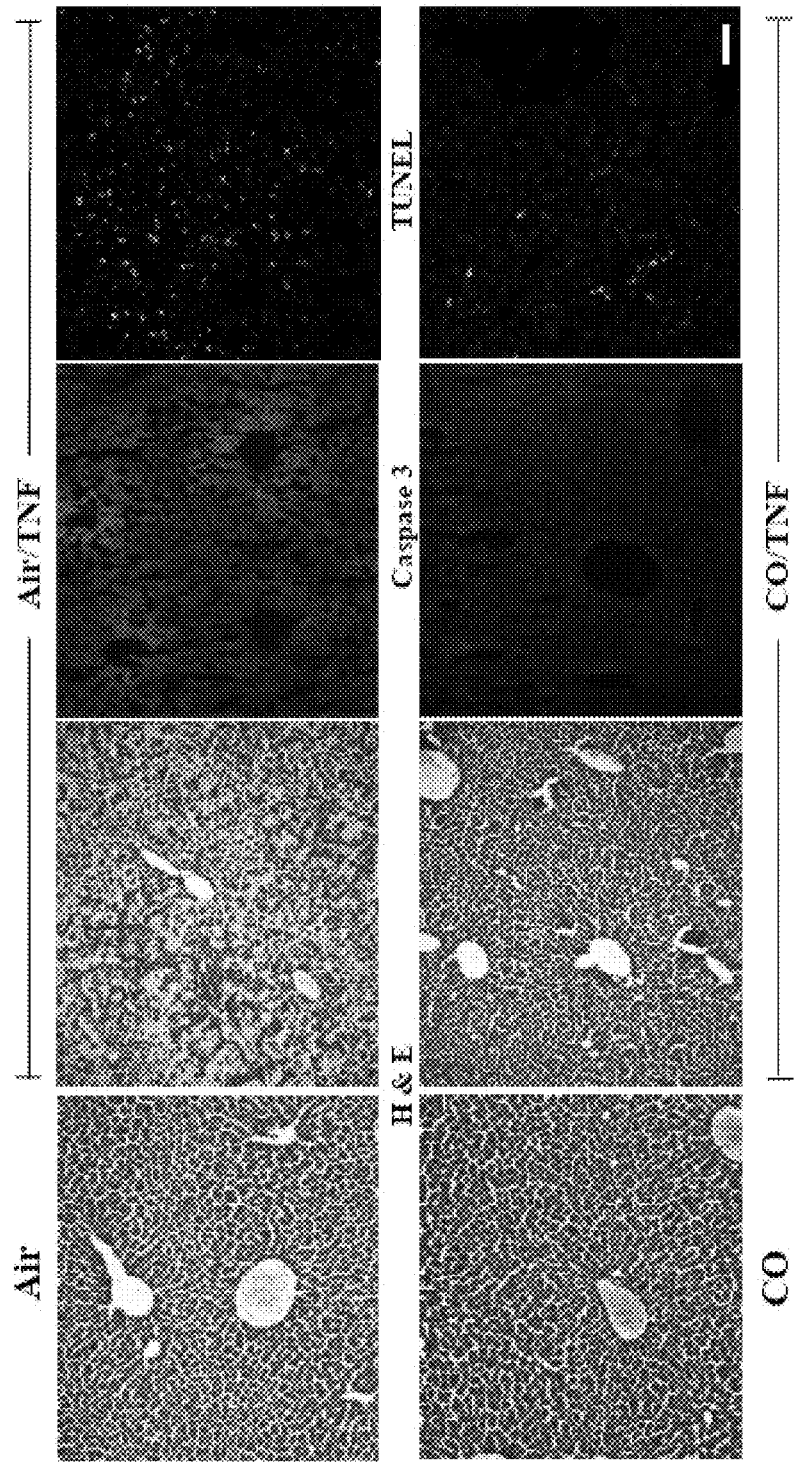
FIGS. 11A-11H are photomicrographs of liver samples illustrating that exogenously-administered CO prevents TNF-α/D-Gal-induced liver injury in mice.

To generate the data presented in FIG. 10, mice were pre-treated with CO (250 ppm) for one hour prior to receiving TNF-α/D-gal (0.3 μg/8 mg/mouse; i.p., respectively). After receiving TNF-α/D-gal, mice were returned to the CO exposure chamber and their serum was analyzed for ALT levels 6-8 hr later. Without exposure to CO, liver failure occurred in 6-8 hr driven primarily by apoptosis of hepatocytes as in the in vitro model described above. Serum ALT in mice treated with CO was 74% lower than in air-exposed mice.

To generate the data presented in FIGS. 11A-11H, liver samples from mice treated with TNF-α/D-gal in the presence and absence of CO (250 ppm) for 8 hr were sectioned and stained for hematoxylin & eosin (H&E), activated caspase 3 (as indicated by an increase in red intensity), and for TUNEL positive cells (as demarcated by the increased green cellular staining; a marker of cell death). Nuclei stained blue. Exposure to CO markedly reduced TNF-α/D-gal-induced liver damage as assessed by H&E staining Livers from mice exposed to CO also displayed fewer TUNEL positive cells, displayed less staining of activated caspase-3, and had normal architecture. Air-exposed control mice that received TNF-α/D-gal showed marked hepatic inflammation, edema, hemorrhage and loss of architecture.

Results discussed above were confirmed using lipopolysaccharide (LPS, also referred to as endotoxin) in place of TNF. In these confirmatory studies, LPS/D-Gal administration resulted in an increase in serum ALT levels from a control level of 20+/−5 IU/ml to >1000 IU/ml, as measured 8 hours following LPS/D-Gal administration. In mice pre-treated with 250 ppm CO, the increase in ALT was reduced by >75%, to 250+/−75 IU/ml. To further characterize the effects observed with CO in this model, serum interleukin-6 was measured, and found to be reduced 65% in animals breathing CO vs air-breathing controls (data not shown). Tissue histopathology of the livers from these mice was similar to that demonstrated using TNF/D-Gal. Untreated and CO-treated mice (no LPS/D-Gal) had no signs of injury while those treated with air and LPS/D-Gal showed marked injury including edema, hemorrhage, neutrophil infiltration and an overall destruction of normal morphology and architecture. In contrast, livers from mice treated with CO and LPS/D-Gal were protected to the same extent as mice treated with CO and TNF/D-Gal. Few changes in the markers of inflammation (edema, hemorrhage, neutrophil infiltration) were observed. Architecture was maintained and appeared grossly similar to untreated and CO (in the absence of LPS/D-Gal)-treated mice. Overall, the use of LPS/D-Gal to induce acute hepatitis paralleled and confirmed data generated using TNF/D-Gal treatment.

The Role of iNOS in CO Protection Against Liver Damage

Whether hepatic iNOS protein levels were increased in the livers of CO-exposed mice after treatment with TNF-α/D-gal was investigated using immunoblotting techniques and immunohistochemistry. Further, whether CO would protect inos$^{-/-}$ mice or wild type mice treated with the selective iNOS inhibitor L-NIL (10 mg/kg, i.p; dosed every 2 hours) was investigated to determine whether iNOS expression has a functional role. The results are provided in FIGS. 12, 13A-13D, and 14.

Figure 12:
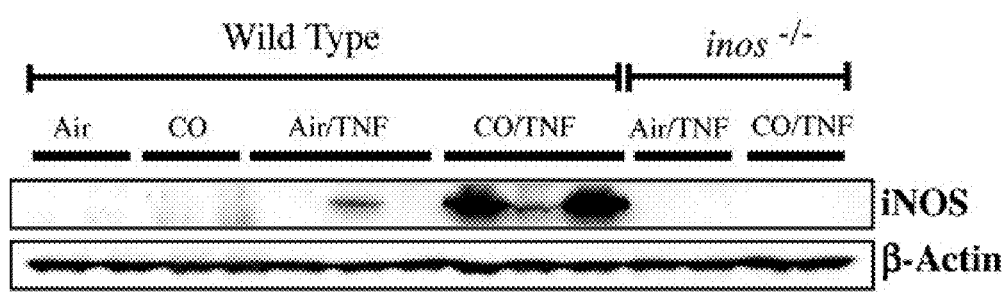
FIG. 12 is a picture of a Western blot illustrating that livers of mice exposed to TNF-α/D-Gal and treated with inhaled CO display increased iNOS protein levels. Wild type=wild type mice; iNOS$^{-/-}$=iNOS deficient mice; CO=carbon monoxide; Air=room air; TNF=TNF-α/D-Gal; β-Actin=control protein.

To generate the data presented in FIG. 12, male C57BL/6J mice were treated with air or CO (250 ppm) 1 hr prior to TNF-α/D-gal (0.3 μg/8 mg/mouse, i.p., respectively) administration. Six hours later, livers were harvested to evaluate iNOS expression by immunoblotting. Results show that iNOS expression was increased modestly in air/TNF-α/D-gal-treated mice, but was markedly increased in mice treated with TNF-α/D-gal and CO. As expected, inos$^{-/-}$ mice showed no expression of iNOS protein.

To generate the data in FIGS. 13A-13D, mouse liver sections were immunostained for iNOS expression. The liver sections were obtained from mice treated with TNF-α/D-gal in the presence or absence of CO, and from air and CO controls that received no TNF-α/D-gal. Livers from mice exposed to CO and not receiving TNF-α/D-gal displayed a modest increase in iNOS expression. However, a significantly greater increase in expression (indicated by an increase in green-stained cells) was observed in livers from mice that were exposed to CO and received TNF-α/D-gal. The increased expression appeared to be localized around blood vessels.

Figure 14:
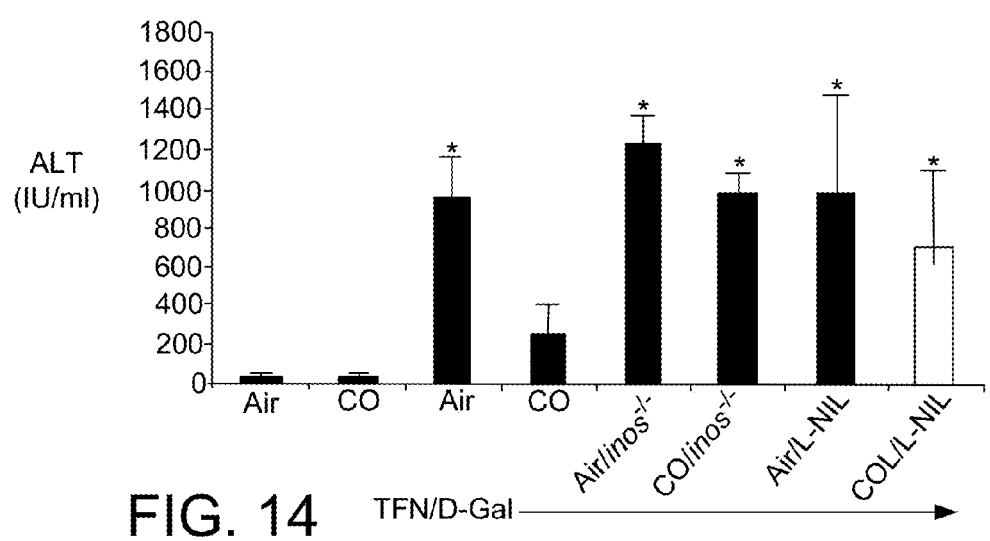
FIG. 14 is a bar graph illustrating that CO does not protect against liver damage in the absence of iNOS function/expression. L-NIL=L-N6-(1-iminoethyl)-lysine-dihydrochloride (a selective inhibitor of iNOS); CO=carbon monoxide; Air=room air; TNF=TNF-α/D-Gal. Results are mean±SD of 6-8 animals/group. *$p<0.01$ versus CO/TNF-α/D-gal and air and CO controls.

To generate the data in FIG. 14, the efficacy of CO-induced protection was tested in the absence of iNOS activity using inos$^{-/-}$ and wild type mice that were treated with L-NIL, the selective inhibitor of iNOS (L-NIL; 5 mg/kg, i.p. dosed every two hours). L-NIL was administered 2 hr prior to CO. CO-treated animals were then pre-treated (250 ppm) for 1 hr prior to TNF-α/D-gal. In the absence of iNOS function/expression, CO is unable to protect against liver damage as assessed by serum ALT levels and histopathology (data not shown).

Thus, it appears the protective effect of inhaled CO in TNF-α-induced liver failure is dependent upon iNOS activity.

The Role of HO-1 in CO Protection Against Acute Liver Failure

Whether CO and NO exert protection against acute liver failure through an HO-1-dependent mechanism was investigated. The data are presented in FIGS. 15, 16, 17, and 18.

Figure 15:
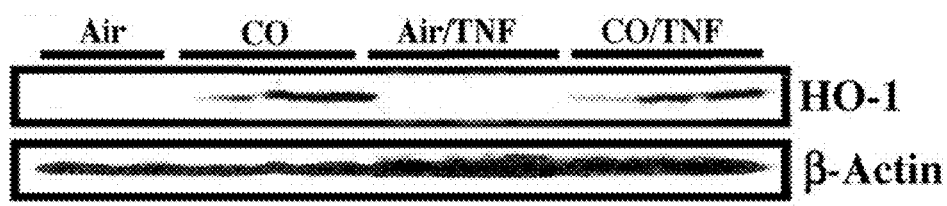
FIG. 15 is a picture of a Western blot illustrating that the livers of CO-treated mice displayed increased expression of HO-1 in both the presence and absence of TNF-α/D-Gal. CO=carbon monoxide; Air=room air; TNF=TNF-α/D-Gal; β-Actin=control protein. Blot is representative of 2 independent experiments.

To generate the data presented in FIG. 15, immunoblotting was performed to observe HO-1 expression in the livers of mice that received TNF-α/D-gal in the presence and absence of CO (250 ppm). CO-treated mice showed a significant increase in HO-1 expression in both the presence and absence of TNF-α/D-gal.

To assess the role of iNOS on TNF-α/D-gal-induced HO-1 expression in the liver (data presented in FIG. 16), mice were administered L-NIL (5 mg/kg, i.p.) 2 hr prior to pre-treatment with CO (250 ppm) and every 2 hr thereafter. Control mice received L-NIL and remained in room air. Note in FIG. 16 that CO increased HO-1 expression in vehicle-treated mice, but was unable to induce expression when iNOS was inhibited. L-NIL treatment alone had a minimal effect on HO-1 expression.

To test the protective role of CO-induced HO-1 (data presented in FIG. 17), mice were given SnPP (50 μmol/kg, s.c.), the selective inhibitor of HO-1, 5 hr prior to CO. Alternatively, the mice were given VPYRRO (VP), an NO donor (10 mg/kg, s.c.). VP was selectively designed to deliver NO directly to the liver. One hour after the initial VP dose, the animals were exposed to CO for 1 hr prior to administration of TNF-α/D-gal (see above). Serum ALT levels were determined 6-8 hr later. Note that CO was not able to provide protection in animals where HO-1 activity was blocked. VP, when administered 2 hr prior and then every 2 hr thereafter, provided protection against injury as determined 8 hour later by serum ALT measurements.

Figure 18:
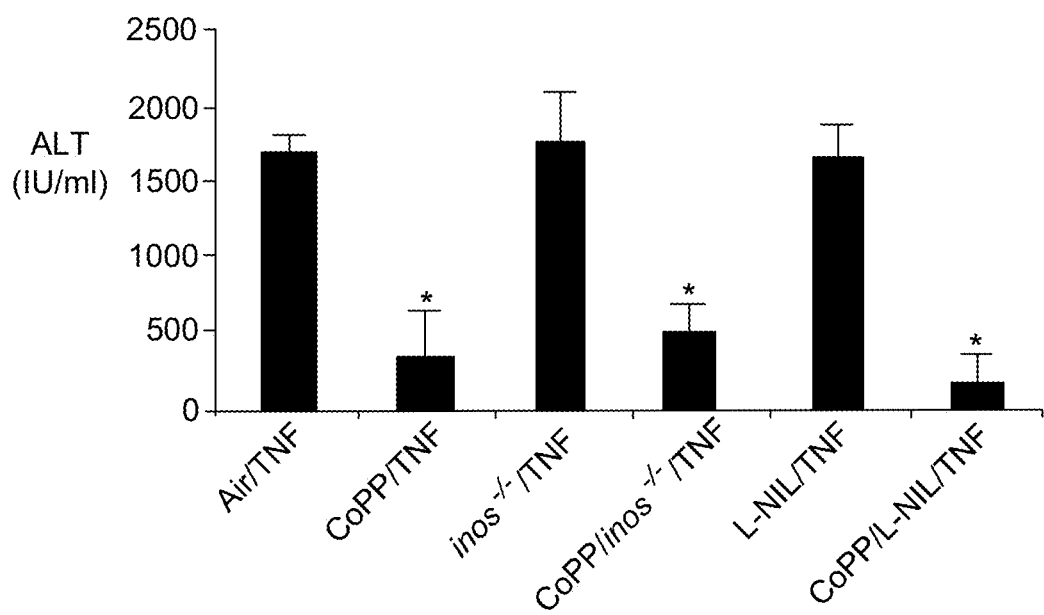
FIG. 18 is a bar graph illustrating that induction of HO-1 is protective against TNF-α-induced liver injury independent of iNOS activity. ALT=serum alanine aminotransferase; Air=room air; TNF=TNF-α/D-Gal; L-NIL=L-N6-(1-iminoethyl)-lysine-dihydrochloride (a selective inhibitor of iNOS); CoPP=cobalt protoporphyrin (an inducer of HO-1); iNOS=iNOS deficient mice. Results are mean±SD of 6-8 mice/group. *$p<0.001$ versus Air/TNF and L-NIL/TNF.

To generate the data presented in FIG. 18, wild type C57BL/6J mice were pretreated for 24 hr with L-NIL in the drinking water (4.5 mM) as described in Stenger et al. (J. Exp. Med. 183: 1501-1514 (1996)). These mice and inos$^{-/-}$ mice were then administered CoPP. L-NIL was maintained in the water throughout the experiment. Control and inos$^{-/-}$ mice received normal drinking water. Twenty-four hr after administration of CoPP, TNF-α/D-gal was administered and serum ALT determined 6-8 hr later. Note in FIG. 18 that induction of HO-1 provides protection regardless of the presence of iNOS.

Figure 16:
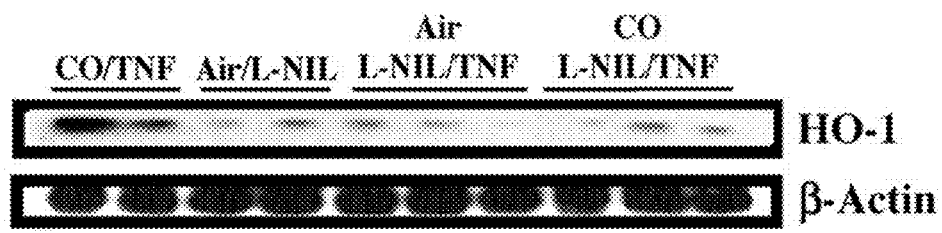
FIG. 16 is a picture of a Western blot illustrating that the livers of CO-treated mice do not display increased expression of HO-1 in the presence or absence of TNF-α/D-Gal if iNOS is inhibited using L-NIL. CO=carbon monoxide; Air=room air; TNF=TNF-α/D-Gal; β-Actin=control protein; L-NIL=L-N6-(1-iminoethyl)-lysine-dihydrochloride (a selective inhibitor of iNOS). Blot is representative of 2 independent experiments.
Figure 17:
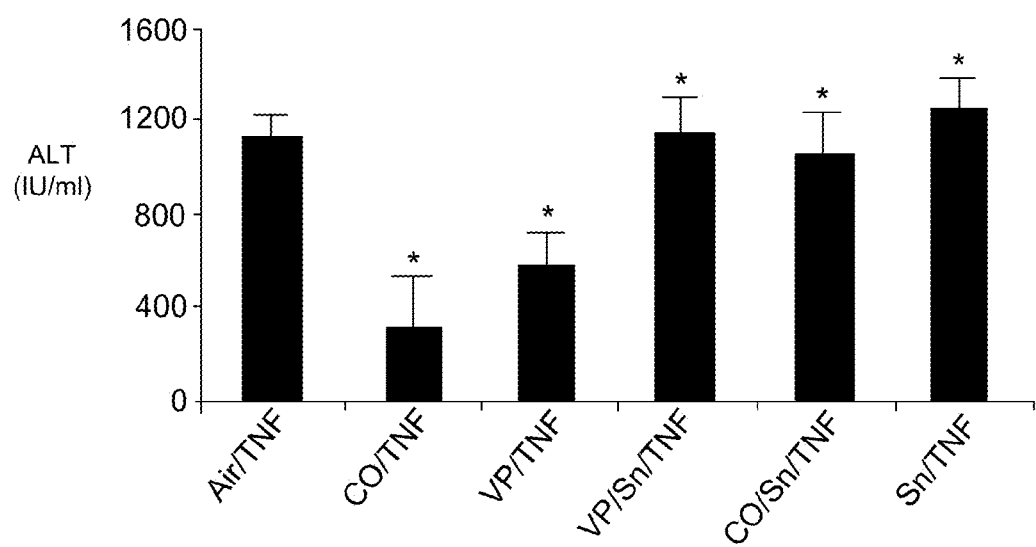
FIG. 17 is a bar graph illustrating that CO-induced HO-1 is protective against TNF-α-induced liver damage in mice. ALT=serum alanine aminotransferase; Air=room air; TNF=TNF-α/D-Gal; Sn=tin protoporphyrin (an inhibitor of HO-1); VP=V-PYRRO (a nitric oxide donor). Results are expressed as mean±SD of 8-10 mice/group. *$p<0.05$ versus CO/TNF/D-gal-treated mice.

Immunoblotting of liver extracts from mice treated with CO in the presence or absence of TNF-α/D-gal showed up-regulation of HO-1 (FIG. 15). The addition of the iNOS inhibitor L-NIL to these above groups, which abrogated the protection (FIG. 17), also prevented up-regulation of HO-1 (FIG. 16). To determine whether HO-1 was central to CO-elicited hepatoprotection, tin protoporphyrin-IX (SnPP, 50 μmol/kg, s.c., Frontier Scientific) was used as a selective inhibitor of HO-1 activity. SnPP significantly diminished the protective effects of CO in this model (FIG. 17). SnPP administration in the absence of TNF-α/D-gal had no deleterious or protective effects (data not shown). These results suggest that up-regulation of HO-1 is important to the protective effects of CO.

To determine if up-regulation of HO-1 would also be needed if protection was initiated by NO, mice were treated with the pharmacological NO donor V-PYRRO/NO. This agent is metabolized by the liver, resulting in release of NO by hepatocytes. V-PYRRO/NO also provides protection following LPS/D-gal or TNF-α/D-gal administration. Mice were randomized and treated with TNF-α/D-gal with or without SnPP to evaluate the role of HO-1. V-PYYRO/NO was protective, as assayed by serum ALT. However, SnPP abrogated the ability of this NO donor to protect against liver damage (FIG. 17). Thus, it appears that CO- or NO-initiated hepatoprotection is at least partially dependent on HO-1.

Because these data suggest that CO and NO require HO-1 activity to protect against TNF-α-induced hepatocyte death, whether protection mediated by HO-1 requires iNOS activity was investigated. Using inos$^{-/-}$ mice, HO-1 was induced via administration of CoPP. TNF-α/D-gal was injected 24 hr thereafter, at the peak of HO-1 expression, and liver damage was assessed 6-8 hr later. The results show that induction of HO-1 was able to significantly prevent liver injury independently of iNOS activity with a >50% reduction in serum ALT (FIG. 18). These results were confirmed using L-NIL. Mice were pre-treated with drinking water containing L-NIL (4.5 mM) for 24 hours. This method effectively inhibits NOS activity. Control mice received normal water. Subsequently, CoPP was administered to induce HO-1 expression and 24 hours thereafter mice were challenged with TNF-α/D-gal. L-NIL treatment alone did not change the severity of injury induced in this model. All animals receiving CoPP (with and without L-NIL) were protected from liver injury (FIG. 18).

Whether HO-1 expression is required for CO- or NO-induced protection from TNF-α/ActD-induced hepatocyte cell death was investigated. The data are presented in FIGS. 19 and 20.

Figure 19:
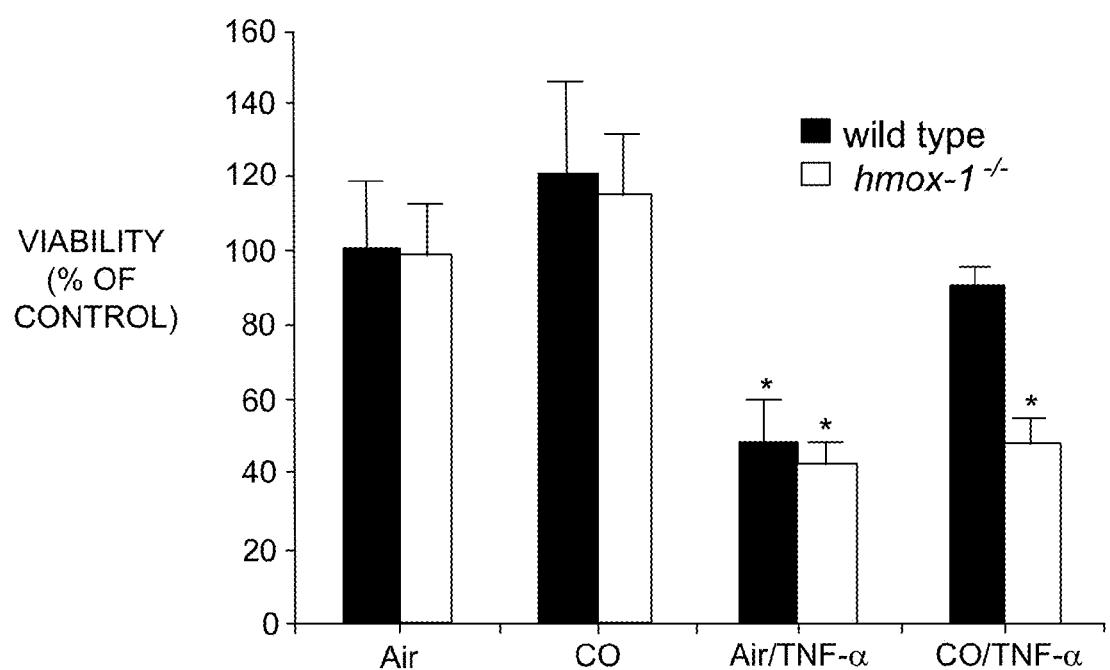
FIG. 19 is bar graph illustrating that HO-1 expression is required for CO-induced protection of mouse hepatocytes from TNF-α/ActD-induced cell death. Wild type (black bars)=hepatocytes isolated from wild type C57BL/6J mice; hmox-1$^{-/-}$ (white bars)=hepatocytes isolated from HO-1 null mice; CO=carbon monoxide; Air=room air; TNF-α=TNF-α/ActD. *$p<0.01$ versus non-TNF-α/ActD treated cells and versus TNF-α/ActD-treated cells that were also treated with CO.

To generate the data presented in FIG. 19, mouse hepatocytes were isolated from HO-1 null mice (hmox-1$^{-/-}$) and wild type (C57BL/6J) littermates, pretreated for 1 hour with CO (250 ppm), and treated with TNF-α/ActD. Viability was assayed as described above. CO significantly protected wild type hepatocytes, but was unable to protect hepatocytes isolated from hmox-1−/− mice.

To generate the data presented in FIG. 20, mouse hepatocytes were isolated from HO-1 null mice (hmox-1$^{-/-}$) and wild type (C57BL/6J) littermates, pretreated with the NO donor SNAP (500 µM), and then treated with TNF-α/ActD 1 hour later. SNAP has been demonstrated to protect hepatocytes in this model. SNAP significantly protected against cell death in wild type hepatocytes but did not provide significant protection against cell death in hepatocytes isolated from hmox-1$^{-/-}$ mice.

Figure 20:
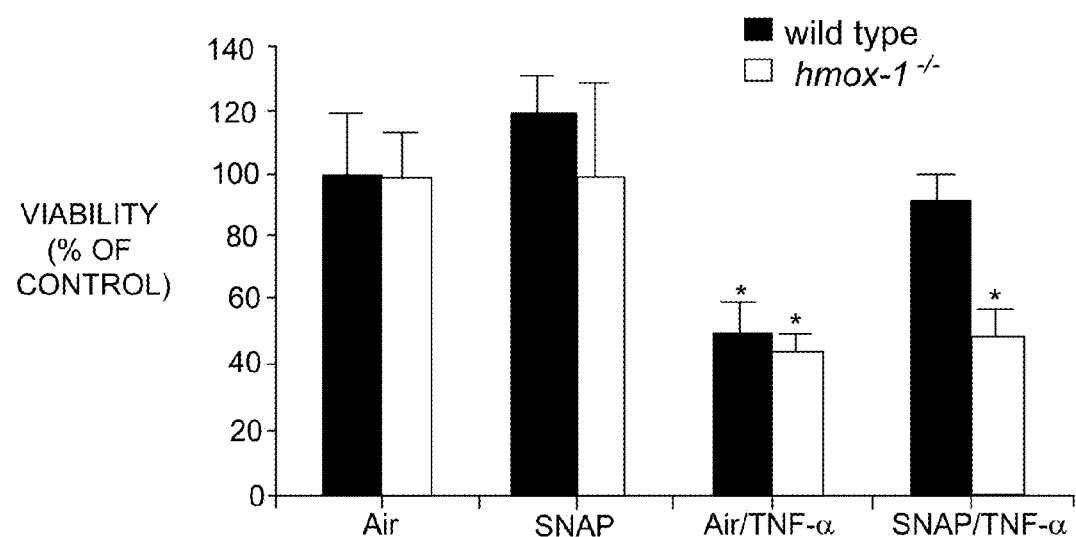
FIG. 20 is bar graph illustrating that HO-1 expression is required for NO-induced protection of mouse hepatocytes from TNF-α/ActD-induced cell death. Wild type (black bars)=hepatocytes isolated from wild type C57BL/6J mice; hmox-1$^{-/-}$ (white bars)=hepatocytes isolated from HO-1 null mice; SNAP=s-nitroso-N-acetyl-penicillamine (an NO donor); Air=room air; TNF-α=TNF-α/ActD. *$p<0.01$ versus non-TNF-α/ActD treated cells and versus TNF-α/ActD-treated cells that were also treated with NO.

As discussed above, air-treated wild type and hmox-1 cells exposed to TNF-α/ActD underwent cell death as expected, while CO- or NO-treated wild type cells were protected in the presence of TNF-α/ActD (FIGS. 19 and 20). The protection conferred by CO and NO was lost in cells lacking functional HO-1 (hmox-1$^{-/-}$). Thus, it appears that HO-1 can provide protection in this model without the involvement of iNOS, suggesting that HO-1 or one or more of its catalytic products can, in part, exert cytoprotective effects in this model.

Inhaled CO is Protective Against Acetaminophen-Induced Hepatitis

Whether inhaled CO is protective against acetaminophen (APAP)-induced hepatitis was investigated. The data are presented in FIG. 21.

Figure 21:
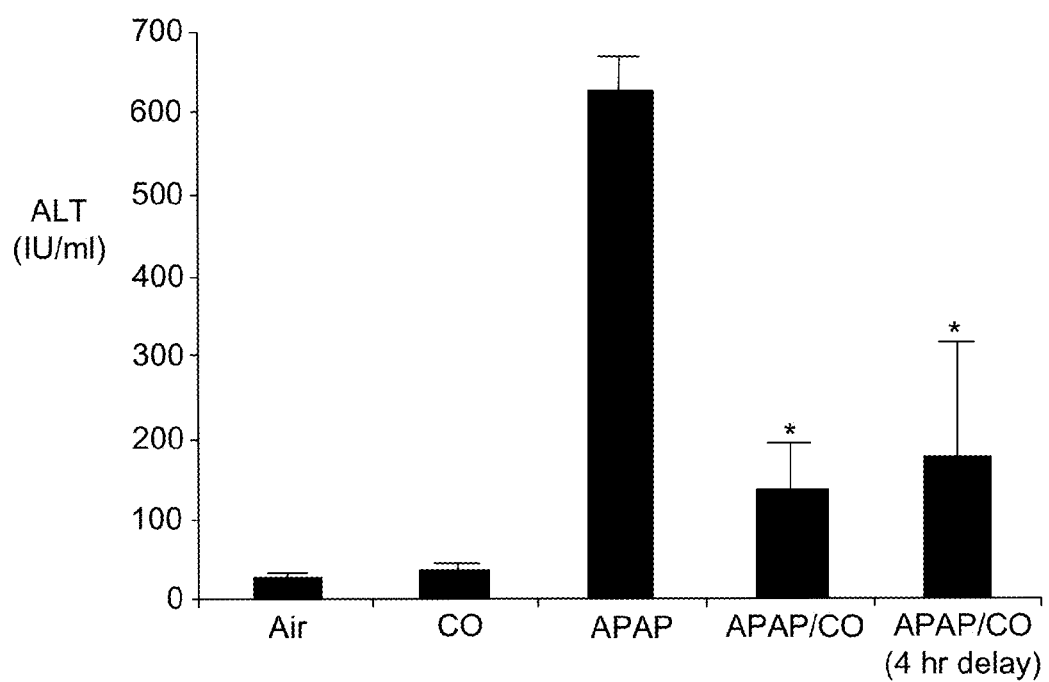
FIG. 21 is a bar graph illustrating that CO-exposed mice were protected from acetaminophen-induced liver injury. ALT=serum alanine aminotransferase; Air=room air; APAP=acetaminophen. Results are mean±SD of 4-8 mice/group.

To generate the data in FIG. 21, Male C57BL/6J mice were exposed to CO (250 ppm) either 1 hr prior or 4 hr post administration of APAP (500 mg/kg, i.p.). The mice were then maintained in CO for the duration of the experiment. Serum ALT levels were determined 20 hr after APAP administration. Control mice received APAP and were maintained in air. This protocol was designed to allow hepatitis to develop for four hours before administering CO. CO significantly reduced damage to the liver as assessed by serum ALT (622±44 vs 175±137, p<0.01 as compared to controls). This protection was similar to that observed in a separate group of animals that had been pre-treated with CO prior to APAP. These data support the therapeutic use of CO in a clinically relevant situation where treatment would begin after the initiation of hepatitis.

The results discussed in this Example demonstrate that a low concentration of CO can protect against TNF-α/D-gal-induced fulminant hepatitis and illustrate a unique and previously unrecognized dependence on both HO-1 and iNOS in the CO-induced protection of livers from damage by TNF-α/D-gal.

Without intending to be bound by theory, it is possible that CO mediated protection operates by activating NF-κB, which in the presence of an inflammatory stimulus leads to the up-regulation of iNOS with the consequent production of NO. In addition to the induction of iNOS, other NF-κB dependent antiapoptotic/protective genes may be induced. During the 1 hour pre-treatment with CO and before the cells are treated with TNF-α, significant activation of NF-κB was present, which could be part of the priming of the cellular apparatus discussed above. The activation of NF-κB by CO may in part result from a mild increase in reactive oxygen species generation originating from the mitochondria (preliminary observations). One hour might also permit time for expression of NF-κB-dependent anti-apoptotic genes. The next step in such a hypothetical model might lead to NO production following the up-regulation of iNOS. NO leads to up-regulation of HO-1, the activity of which confers protective effects. The protective effect of HO-1 could be due to removal of heme or to any one or more of its three products: CO, biliverdin/bilirubin or iron/ferritin. Given that exogenous CO was administered throughout the duration of the experiments, it appears unlikely that endogenously-produced CO alone mediates HO-1 protection. However, the combination of CO with other products of HO-1 or these other products acting individually might be involved.

In a study described above, CO was administered in a clinically-relevant model of acetaminophen (APAP)-induced hepatitis that has a time course that is similar to the development of acute hepatitis in humans. The data demonstrate that exposure to CO 4 hours after administration of APAP (500 mg/kg, i.p.) resulted in a 62% reduction in liver injury (FIG. 21). In this model of APAP-induced liver injury, mice show signs of hepatitis as early as 2-4 hours after APAP administration and lethality occurs by 24-48 hours. Thus, CO was administered after the initiation of liver injury. Consistent with the data in the APAP model are the results in a murine model of hemorrhagic shock where the therapeutic initiation of inhaled CO during resuscitation following a 2.5 hour shock phase resulted in protection against liver injury (>65% reduction in serum ALT at 24 hr p<0.01; n=6-10/group).

In summary, employing a model of liver injury driven principally by TNF-α-induced apoptosis, the following was demonstrated: first, inhaled CO can prevent hepatitis in this model; second, protection by CO requires generation of a second gaseous molecule, NO; third, NO exerts its beneficial effects, at least in part, via upregulation of HO-1; and fourth, up-regulation of HO-1 is protective without a need for iNOS/NO activity, i.e., without an obligate continuation of the cycle.

EXAMPLE 2

Protocol for the Treatment of Hepatitis

The following example illustrates protocols for use in treating a patient diagnosed as suffering from hepatitis. The example also illustrates protocols for treating patients before, during, and/or after surgical procedures, e.g., a surgical procedure to transplant a liver. Skilled practitioners will appreciate that any protocol described herein can be adapted based on a patient's individual needs, and can be adapted to be used in conjunction with any other treatment for hepatitis.

Treatment of Patients

Treatment of a patient with CO can begin on the day the patient is diagnosed as suffering from hepatitis, for example, hepatitis caused by viral infection and/or alcohol abuse. The patient can be diagnosed by a physician using any art-known method. For example, a physician may make such a diagnosis using data obtained from blood tests, e.g., tests to determine serum ALT levels and tests to determine whether a patient is infected with a particular virus (e.g., any known hepatitis virus). Further, a physician may consider a patient's medical history in making such a diagnosis (e.g., by considering whether a patient is an alcoholic or a chronic drug user). The patient can inhale CO at concentration of about 250 to 500 ppm for one hour per day. This treatment can continue for about 30 days, or until the patient is diagnosed as no longer having or being at risk for hepatitis.

Liver Transplant Procedures

Treatment of a Liver Donor

Prior to harvesting a liver or portion thereof, the donor can be treated with inhaled carbon monoxide (250 ppm) for one hour. Treatment can be administered at doses varying from 10 ppm to 1000 ppm for times varying from one hour to six hours, or for the entire period from the moment when it becomes possible to treat a brain-dead (cadaver) donor to the time the organ is removed. For a human donor, treatment should start as soon as possible following the declaration that brain death is present. In some applications, it may be desirable to begin treatment before brain death.

For non-human animals (e.g., pigs) to be used as xenotransplantation donors, the live donor animal can be treated with relatively high levels of inhaled carbon monoxide, as desired, so long as the carboxyhemoglobin so produced does not compromise the viability and function of the organ to be transplanted. For example, one could use levels greater than 500 ppm (e.g., 1000 ppm or higher, and up to 10,000 ppm, particularly for brief times).

Treatment of the Liver In Situ

Before a liver is harvested from a donor, it can be flushed or perfused with a solution, e.g., a buffer or medium, while it is still in the donor. The intent is to flush the liver with a solution saturated with carbon monoxide and maintained in a carbon monoxide atmosphere so that the carbon monoxide content remains at saturation. Flushing can take place for a time period of at least 10 minutes, e.g., 1 hour, several hours, or longer. The solution should ideally deliver the highest concentration of carbon monoxide possible to the cells of the liver (or portion thereof).

Treatment of the Liver Ex Vivo

A liver can be preserved in a medium that includes carbon monoxide from the time it is removed from the donor to the time it is transplanted to the recipient. This can be performed by maintaining the liver in the medium comprising CO, or by perfusing it with such a medium. Since this occurs ex vivo rather than in an animal, very high concentrations of CO gas can be used (e.g., 10,000 ppm) to keep the medium saturated with CO.

Treatment of a Liver Recipient

Treatment of the recipient with CO can begin on the day of transplantation at least 30 minutes before surgery begins. Alternatively, it could begin at least 30 minutes before re-perfusion of the organ in the recipient. It can be continued for at least 30 minutes, e.g., 1 hour. Carbon monoxide doses between 10 ppm and 3000 ppm can be delivered for varying times, e.g., minutes or hours, and can be administered on the day of and on days following transplantation. For example, the patient can inhale a concentration of carbon monoxide, e.g., 3000 ppm, for three consecutive 10 second breath holds. Alternatively, a lower concentration of the gas can be delivered intermittently or constantly, for a longer period of time, with regular breathing rather than breath holding. Carboxyhemoglobin concentrations can be utilized as a guide for appropriate administration of carbon monoxide to a patient. Usually, treatments for recipients should not raise carboxyhemoglobin levels above those considered to pose an acceptable risk for a patient in need of a transplant.

A number of embodiments of the invention have been described. Nevertheless, it will be understood that various modifications may be made without departing from the spirit and scope of the invention. Accordingly, other embodiments are within the scope of the following claims.

---

---

What is claimed is:

1. A method of treating hepatitis in a patient at risk of acute liver failure, comprising:

identifying a patient diagnosed as suffering from hepatitis that is not a post-operative result of liver transplantation, and who is at risk of acute liver failure; and administering to the patient by inhalation a gaseous pharmaceutical composition comprising from 100 ppm to 800 ppm of carbon monoxide for up to six hours per day to reduce hepatocyte death in the patient.

2. The method of claim 1, wherein the patient is infected with a virus selected from the group consisting of: hepatitis A virus, hepatitis B virus, hepatitis C virus, hepatitis D virus, hepatitis E virus, and hepatitis G virus.

3. The method of claim 1, wherein the patient is an alcoholic.

4. The method of claim 1, further comprising administering antiviral agents to the patient.

5. The method of claim 1, wherein the hepatitis is caused by exposure to a hepatotoxic agent.

6. The method of claim 1, wherein administering the gaseous composition comprising carbon monoxide comprises:
   providing a vessel containing a pressurized gas comprising carbon monoxide gas;
   releasing the pressurized gas from the vessel, to form an atmosphere comprising carbon monoxide gas; and
   exposing the patient to the atmosphere.

7. The method of claim 1, further comprising withholding or reducing administration of hepatitis-inducing drugs.

8. The method of claim 1, further comprising administering corticosteroids to the patient.

\* \* \* \* \*

UNITED STATES PATENT AND TRADEMARK OFFICE
CERTIFICATE OF CORRECTION

PATENT NO. : 9,522,163 B2
APPLICATION NO. : 14/094140
DATED : December 20, 2016
INVENTOR(S) : Leo E. Otterbein, Augustine M. K. Choi and Brian Scott Zuckerbraun It is certified that error appears in the above-identified patent and that said Letters Patent is hereby corrected as shown below:

In the Specification

Column 1
Line 18, delete "U.S. Government" and insert -- government --
Lines 19-20, delete "National Institutes of Health Grant Nos. R01-GM-44100, HL 58688, HL55330, HL60234, and AI42365." and insert -- grant numbers GM044100, HL058688, HL055330, HL060234, and AI042365 awarded by the National Institutes of Health. --
Line 21, delete "Government" and insert -- government --
Line 21, delete "this invention." and insert -- the invention. --

Signed and Sealed this
Sixth Day of November, 2018

Andrei Iancu
*Director of the United States Patent and Trademark Office*